United States Patent
Hollis et al.

(10) Patent No.: US 12,403,012 B2
(45) Date of Patent: Sep. 2, 2025

(54) BONE REPOSITIONING GUIDE SYSTEM AND PROCEDURE

(71) Applicant: CrossRoads Extremity Systems, LLC, Memphis, TN (US)

(72) Inventors: Chad Hollis, Collierville, TN (US); Daniel Sayger, Southaven, MS (US)

(73) Assignee: CrossRoads Extremity Systems, LLC, Memphis, TN (US)

( * ) Notice: Subject to any disclaimer, the term of this patent is extended or adjusted under 35 U.S.C. 154(b) by 294 days.

(21) Appl. No.: 17/629,754

(22) PCT Filed: Jul. 24, 2020

(86) PCT No.: PCT/US2020/043525
§ 371 (c)(1),
(2) Date: Jan. 24, 2022

(87) PCT Pub. No.: WO2021/021640
PCT Pub. Date: Feb. 4, 2021

(65) Prior Publication Data
US 2022/0249143 A1    Aug. 11, 2022

Related U.S. Application Data

(60) Provisional application No. 62/879,340, filed on Jul. 26, 2019.

(51) Int. Cl.
*A61F 2/42* (2006.01)
*A61B 17/064* (2006.01)
(Continued)

(52) U.S. Cl.
CPC .......... *A61F 2/4225* (2013.01); *A61B 17/151* (2013.01); *A61B 17/1697* (2013.01);
(Continued)

(58) Field of Classification Search
CPC ........ A61B 2017/564; A61B 2017/565; A61B 2017/568; A61B 2017/681; A61B 17/17;
(Continued)

(56) References Cited

U.S. PATENT DOCUMENTS

| 4,069,824 A | 1/1978 | Weinstock |
| 4,335,715 A | 6/1982 | Kirkley |

(Continued)

FOREIGN PATENT DOCUMENTS

| EP | 0570187 A1 | 11/1993 |
| JP | 2006-346447 A | 12/2006 |

(Continued)

OTHER PUBLICATIONS

Arthrex Hallux Valgus Solutions, Arthrex, Inc., www.arthrex.com 2009, 2 pp.

(Continued)

*Primary Examiner* — Marcela I. Shirsat
(74) *Attorney, Agent, or Firm* — BakerHostetler

(57) ABSTRACT

An improved surgical system and procedure for correcting a deformity between first and second bones using an alignment guide based on a correction factor. The correction factor can be based on a virtual model of the first and second bones in a deformed configuration and a corrected configuration. In the virtual corrected configuration, first and second virtual axes can be fixed in the respective first and second bones. When reverted to the virtual deformed configuration, the orientation of the first and second axes can be used to determine the correction factor. The alignment guide is used to insert one or more k-wires into each of the first and second bones in a deformed configuration. A correction guide is passed along the k-wires to rotate and/or translate the first bone relative to the second bone into the corrected configuration.

19 Claims, 33 Drawing Sheets

(51) Int. Cl.
  *A61B 17/15* (2006.01)
  *A61B 17/16* (2006.01)
  *A61B 17/17* (2006.01)
  *A61B 17/56* (2006.01)
  *A61B 17/68* (2006.01)
  *A61B 17/80* (2006.01)
  *A61B 17/84* (2006.01)
  *A61F 2/46* (2006.01)

(52) U.S. Cl.
  CPC .......... *A61B 17/1775* (2016.11); *A61B 17/56* (2013.01); *A61B 17/8061* (2013.01); *A61B 17/808* (2013.01); *A61B 17/848* (2013.01); *A61B 17/0642* (2013.01); *A61B 17/1728* (2013.01); *A61B 17/1739* (2013.01); *A61B 2017/564* (2013.01); *A61B 2017/565* (2013.01); *A61B 2017/681* (2013.01); *A61B 17/8004* (2013.01); *A61F 2002/4228* (2013.01); *A61F 2002/4233* (2013.01); *A61F 2002/4238* (2013.01); *A61F 2/4606* (2013.01)

(58) Field of Classification Search
  CPC ............ A61B 17/1775; A61B 17/1728; A61B 17/1739; A61B 17/15; A61B 17/151; A61B 17/152; A61B 17/1697; A61B 17/56; A61B 17/80; A61B 17/8061; A61B 17/808; A61B 17/848; A61B 17/68; A61B 17/0642; A61B 17/8004; A61B 17/1659; A61B 17/1682; A61F 5/019; A61F 2002/4228; A61F 2002/4233; A61F 2002/4238; A61F 2/4225; A61F 2/4606; A61F 2/4603
  USPC ......... 606/281, 280, 86 R, 87, 98, 103, 104, 606/86 A, 86 B, 914, 915
  See application file for complete search history.

(56) References Cited

U.S. PATENT DOCUMENTS

| | | | |
|---|---|---|---|
| 4,349,018 A | 9/1982 | Chambers | |
| 4,409,973 A | 10/1983 | Neufeld | |
| 4,440,168 A | 4/1984 | Warren | |
| 4,501,268 A | 2/1985 | Comparetto | |
| 4,502,474 A | 3/1985 | Comparetto | |
| 4,509,511 A | 4/1985 | Neufeld | |
| 4,565,191 A | 1/1986 | Slocum | |
| 4,627,425 A | 12/1986 | Reese | |
| 4,632,102 A | 12/1986 | Comparetto | |
| 4,664,102 A | 5/1987 | Comparetto | |
| 4,708,133 A | 11/1987 | Comparetto | |
| 4,736,737 A | 4/1988 | Fargie et al. | |
| 4,750,481 A | 6/1988 | Reese | |
| 4,757,810 A | 7/1988 | Reese | |
| 4,852,558 A * | 8/1989 | Outerbridge | A61B 17/1732 606/75 |
| 4,913,144 A | 4/1990 | Del Medico | |
| 4,952,214 A | 8/1990 | Comparetto | |
| 4,959,066 A | 9/1990 | Dunn et al. | |
| 5,035,698 A | 7/1991 | Comparetto | |
| 5,042,983 A | 8/1991 | Rayhack | |
| 5,049,149 A | 9/1991 | Schmidt | |
| 5,053,039 A | 10/1991 | Hofmann et al. | |
| 5,078,719 A | 1/1992 | Schreiber | |
| 5,112,334 A | 5/1992 | Alchermes et al. | |
| 5,147,364 A | 9/1992 | Comparetto | |
| 5,176,685 A | 1/1993 | Rayhack | |
| 5,246,444 A | 9/1993 | Schreiber | |
| D357,534 S * | 4/1995 | Hayes | D24/140 |
| 5,413,579 A | 5/1995 | Tom Du Toit | |
| 5,449,360 A | 9/1995 | Schreiber | |
| 5,470,335 A | 11/1995 | Du Toit | |
| 5,540,695 A | 7/1996 | Levy | |
| 5,578,038 A * | 11/1996 | Slocum | A61B 17/15 606/86 R |
| 5,601,565 A | 2/1997 | Huebner | |
| 5,613,969 A | 3/1997 | Jenkins, Jr. | |
| 5,620,448 A | 4/1997 | Puddu | |
| 5,643,270 A | 7/1997 | Combs | |
| 5,667,510 A | 9/1997 | Combs | |
| H1706 H | 1/1998 | Mason | |
| 5,722,978 A | 3/1998 | Jenkins, Jr. | |
| 5,749,875 A | 5/1998 | Puddu | |
| 5,779,709 A | 7/1998 | Harris et al. | |
| 5,843,085 A | 12/1998 | Graser | |
| 5,911,724 A | 6/1999 | Wehrli | |
| 5,980,526 A | 11/1999 | Johnson et al. | |
| 5,984,931 A | 11/1999 | Greenfield | |
| 6,007,535 A | 12/1999 | Rayhack et al. | |
| 6,027,504 A | 2/2000 | McGuire | |
| 6,030,391 A | 2/2000 | Brainard et al. | |
| 6,203,545 B1 | 3/2001 | Stoffella | |
| 6,248,109 B1 | 6/2001 | Stoffella | |
| 6,391,031 B1 | 5/2002 | Toomey | |
| 6,547,793 B1 | 4/2003 | McGuire | |
| 6,676,662 B1 | 1/2004 | Bagga et al. | |
| 6,755,838 B2 | 6/2004 | Trnka | |
| 6,796,986 B2 | 9/2004 | Duffner | |
| 7,018,383 B2 | 3/2006 | McGuire | |
| 7,112,204 B2 | 9/2006 | Justin et al. | |
| 7,182,766 B1 | 2/2007 | Mogul | |
| 7,540,874 B2 | 6/2009 | Trumble et al. | |
| 7,572,258 B2 | 8/2009 | Stiernborg | |
| 7,691,108 B2 | 4/2010 | Lavallee | |
| 7,763,026 B2 | 7/2010 | Egger et al. | |
| D630,746 S * | 1/2011 | Richter | D24/140 |
| 7,967,823 B2 | 6/2011 | Ammann et al. | |
| 7,972,338 B2 | 7/2011 | O'Brien | |
| 8,062,301 B2 | 11/2011 | Ammann et al. | |
| 8,083,746 B2 | 12/2011 | Novak | |
| 8,137,406 B2 | 3/2012 | Novak et al. | |
| 8,236,000 B2 | 8/2012 | Ammann et al. | |
| 8,262,664 B2 | 9/2012 | Justin et al. | |
| 8,277,459 B2 | 10/2012 | Sand et al. | |
| 8,282,645 B2 | 10/2012 | Lawrence et al. | |
| 8,313,492 B2 | 11/2012 | Wong et al. | |
| 8,409,209 B2 | 4/2013 | Ammann et al. | |
| 8,496,662 B2 | 7/2013 | Novak et al. | |
| 8,529,571 B2 | 9/2013 | Horan et al. | |
| 8,540,777 B2 | 9/2013 | Ammann et al. | |
| 8,545,508 B2 | 10/2013 | Collazo | |
| D695,402 S | 12/2013 | Dacosta et al. | |
| 8,652,142 B2 | 2/2014 | Geissler | |
| 8,657,820 B2 | 2/2014 | Kubiak et al. | |
| 8,702,715 B2 | 4/2014 | Ammann et al. | |
| 8,771,279 B2 | 7/2014 | Philippon et al. | |
| 8,777,948 B2 | 7/2014 | Bernsteiner | |
| 8,888,785 B2 | 11/2014 | Ammann et al. | |
| 8,900,247 B2 | 12/2014 | Tseng et al. | |
| 8,906,026 B2 | 12/2014 | Ammann et al. | |
| 9,060,822 B2 | 6/2015 | Lewis et al. | |
| 9,113,920 B2 | 8/2015 | Ammann et al. | |
| 9,622,805 B2 | 4/2017 | Santrock et al. | |
| 9,687,250 B2 | 6/2017 | Dayton et al. | |
| 9,814,474 B2 | 11/2017 | Montoya et al. | |
| 9,907,558 B2 | 3/2018 | Fallin et al. | |
| 9,936,994 B2 | 4/2018 | Smith et al. | |
| 10,045,807 B2 | 8/2018 | Santrock et al. | |
| 10,245,086 B2 | 4/2019 | Treace et al. | |
| 10,245,088 B2 | 4/2019 | Dayton et al. | |
| 10,292,713 B2 | 5/2019 | Fallin et al. | |
| 10,335,220 B2 | 7/2019 | Smith et al. | |
| 10,342,590 B2 | 7/2019 | Bays et al. | |
| 10,376,268 B2 | 8/2019 | Fallin et al. | |
| 10,470,779 B2 | 11/2019 | Fallin et al. | |
| 10,512,470 B1 | 12/2019 | Bays et al. | |
| 10,555,757 B2 | 2/2020 | Dayton | |
| 10,561,426 B1 | 2/2020 | Dayton et al. | |
| 10,575,862 B2 | 3/2020 | Bays et al. | |
| 10,743,995 B2 | 8/2020 | Fallin et al. | |
| 10,898,211 B2 | 1/2021 | Fallin et al. | |

(56) References Cited

U.S. PATENT DOCUMENTS

| | | |
|---|---|---|
| 11,058,546 B2 | 7/2021 | Hollis et al. |
| 11,116,558 B2 | 9/2021 | Smith et al. |
| 11,147,590 B2 | 10/2021 | Dayton et al. |
| 11,160,567 B2 | 11/2021 | Fallin et al. |
| 2002/0165552 A1 | 11/2002 | Duffner |
| 2004/0097946 A1 | 5/2004 | Dietzel et al. |
| 2004/0138669 A1 | 7/2004 | Horn |
| 2005/0070909 A1 | 3/2005 | Egger et al. |
| 2005/0149042 A1 | 7/2005 | Metzger |
| 2005/0228389 A1 | 10/2005 | Stiernborg |
| 2005/0251147 A1 | 11/2005 | Novak |
| 2005/0273112 A1 | 12/2005 | McNamara |
| 2006/0129163 A1 | 6/2006 | McGuire |
| 2006/0264961 A1 | 11/2006 | Murray-Brown |
| 2006/0276795 A1 | 12/2006 | Orbay et al. |
| 2007/0010818 A1 | 1/2007 | Stone et al. |
| 2007/0265634 A1 | 11/2007 | Weinstein |
| 2007/0276383 A1 | 11/2007 | Rayhack |
| 2008/0015603 A1 | 1/2008 | Collazo |
| 2008/0039850 A1 | 2/2008 | Rowley et al. |
| 2008/0147073 A1 | 6/2008 | Ammann et al. |
| 2008/0195215 A1 | 8/2008 | Morton |
| 2008/0269908 A1 | 10/2008 | Warburton |
| 2009/0036931 A1 | 2/2009 | Pech et al. |
| 2009/0054899 A1 | 2/2009 | Ammann et al. |
| 2009/0210010 A1 | 8/2009 | Strnad et al. |
| 2009/0222047 A1 | 9/2009 | Graham |
| 2010/0125300 A1 | 5/2010 | Blitz et al. |
| 2010/0130981 A1 | 5/2010 | Richards |
| 2010/0152782 A1 | 6/2010 | Stone et al. |
| 2011/0178524 A1 | 7/2011 | Lawrence et al. |
| 2011/0188550 A1 | 8/2011 | Wajcer et al. |
| 2011/0213376 A1 | 9/2011 | Maxson et al. |
| 2011/0224734 A1 | 9/2011 | Schelling |
| 2012/0016426 A1 | 1/2012 | Robinson |
| 2012/0185056 A1 | 7/2012 | Warburton |
| 2012/0191199 A1 | 7/2012 | Raemisch |
| 2012/0303033 A1 | 11/2012 | Weiner et al. |
| 2013/0012949 A1 | 1/2013 | Fallin et al. |
| 2013/0090662 A1 | 4/2013 | Hanson et al. |
| 2013/0172942 A1 | 7/2013 | Lewis et al. |
| 2013/0184708 A1 | 7/2013 | Robinson et al. |
| 2013/0226248 A1 | 8/2013 | Hatch et al. |
| 2013/0226252 A1 | 8/2013 | Mayer |
| 2013/0317559 A1 | 11/2013 | Leavitt et al. |
| 2013/0331845 A1 | 12/2013 | Horan et al. |
| 2014/0188139 A1 | 7/2014 | Fallin et al. |
| 2014/0194999 A1 | 7/2014 | Orbay et al. |
| 2014/0343555 A1 | 11/2014 | Russi et al. |
| 2015/0057667 A1 | 2/2015 | Ammann et al. |
| 2015/0245858 A1 | 9/2015 | Weiner et al. |
| 2016/0015426 A1 | 1/2016 | Dayton |
| 2016/0135858 A1 | 5/2016 | Dacosta et al. |
| 2016/0192950 A1 | 7/2016 | Dayton et al. |
| 2016/0192970 A1 | 7/2016 | Dayton et al. |
| 2016/0213384 A1 | 7/2016 | Fallin et al. |
| 2016/0235414 A1 | 8/2016 | Hatch et al. |
| 2016/0324532 A1 | 11/2016 | Montoya et al. |
| 2016/0324555 A1 | 11/2016 | Brumfield et al. |
| 2016/0354127 A1 | 12/2016 | Lundquist et al. |
| 2017/0007305 A1 | 1/2017 | Hollis et al. |
| 2017/0014143 A1 | 1/2017 | Dayton et al. |
| 2017/0014173 A1 | 1/2017 | Smith et al. |
| 2017/0042598 A1 | 2/2017 | Santrock et al. |
| 2017/0042599 A1 | 2/2017 | Bays et al. |
| 2017/0049576 A1 | 2/2017 | Guilford et al. |
| 2017/0056031 A1 | 3/2017 | Awtrey et al. |
| 2017/0079669 A1 | 3/2017 | Bays et al. |
| 2017/0156717 A1 | 6/2017 | Triplett et al. |
| 2017/0164989 A1 | 6/2017 | Weiner et al. |
| 2017/0172638 A1 | 6/2017 | Santrock et al. |
| 2017/0196602 A1 | 7/2017 | Lundquist et al. |
| 2018/0110530 A1* | 4/2018 | Wagner ............... A61B 17/151 |
| 2018/0125504 A1 | 5/2018 | Dayton et al. |
| 2018/0296257 A1* | 10/2018 | Penzimer ........... A61B 17/8625 |
| 2019/0125418 A1 | 5/2019 | Muller et al. |
| 2019/0175238 A1 | 6/2019 | Dayton et al. |
| 2019/0274745 A1 | 9/2019 | Smith et al. |
| 2019/0328435 A1 | 10/2019 | Bays et al. |
| 2019/0328436 A1 | 10/2019 | Bays et al. |
| 2019/0357919 A1 | 11/2019 | Fallin et al. |
| 2020/0015856 A1 | 1/2020 | Treace et al. |
| 2020/0078025 A1 | 3/2020 | Fallin et al. |
| 2020/0138491 A1 | 5/2020 | Brigido et al. |
| 2020/0197021 A1 | 6/2020 | Dayton et al. |
| 2020/0375644 A1 | 12/2020 | Smith et al. |
| 2021/0022879 A1 | 1/2021 | Hollis et al. |
| 2021/0026357 A1 | 1/2021 | Okubi et al. |
| 2021/0077162 A1 | 3/2021 | Muller et al. |
| 2021/0077192 A1 | 3/2021 | Perler et al. |
| 2021/0251670 A1 | 8/2021 | Sayger et al. |
| 2021/0282823 A1 | 9/2021 | Day et al. |
| 2021/0307763 A1 | 10/2021 | Fallin et al. |

FOREIGN PATENT DOCUMENTS

| | | |
|---|---|---|
| JP | 2017-047167 A | 3/2017 |
| JP | 2019-024741 A | 2/2019 |
| JP | 2019-080918 A | 5/2019 |
| WO | 00/06036 A1 | 2/2000 |
| WO | 2004/075775 A2 | 9/2004 |
| WO | 2004/089227 A2 | 10/2004 |
| WO | 2005/041785 A1 | 5/2005 |
| WO | 2007/008348 A2 | 1/2007 |
| WO | 2008/097781 A1 | 8/2008 |
| WO | 2016/134154 A1 | 8/2016 |
| WO | 2016/134160 A1 | 8/2016 |
| WO | 2017/011589 A1 | 1/2017 |
| WO | 2017/031000 A1 | 2/2017 |
| WO | 2017/049056 A1 | 3/2017 |
| WO | 2018/081185 A1 | 5/2018 |
| WO | 2021/021640 A1 | 2/2021 |
| WO | 2021/026357 A1 | 2/2021 |
| WO | 2021/167992 A1 | 8/2021 |

OTHER PUBLICATIONS

Comprehensive Solutions for Forefoot and Midfood Sungery using the Mini TightRope System, Arthrex, Inc., www arthrex com 2012, 15 pp.

DiDomenico, Lawrence A., et al. "Lapidus Bunionectomy: First Metatarsal-Cuneiform Arthrodesis," Souhterland, Chapter 31, Aug. 18, 2012.

Distal Extremities Orthopaedic Update, Arthrex, Inc., www.arthrex.com, 2014, 24 pp.

Dobbe, et al, "Computer-Assisted and Patent-Specific 3-D Planning and Evaluation of a Single-Cut Rotational Osteotomy for Complex long-Bone Deformities". Med Biol Eng Comput (2011) 49:1363-1370.

Foot & Ankle Repair and Reconstruction Technology Brochure, Arthrex, Inc., www.athrex.com, 2016, 86 pp.

Gregg, Julie, et al., "Plantar Plate Repair and Weil Osteotomy for Meteatarsophalangeal Joint Instability", Foot and Ankle Surgery 13(2007) 116-121.

International Search Report and Written Opinion dated Jul. 22, 2021 in application No. PCT/US21/18398.

International Search Report and Written Opinion for PCT Application No. PCT/US2020/043525 dated Dec. 7, 2020 in 22 pages.

Meyer, D.C., et al., "A New Methodology for the Planning of Single Cut Corrective Osteotornles of Mai-Aligned Long Bones", Clinical Blornechanics 20(2005) 223-227.

Oscillating Saw Attachment fo, EPD/APD, Colibri II and Small Electric Drive, Synthes GmbH, www.synthes.com, 2012, 2 pp.

Scarf Osteotomy Technical Information Sheet, TALUS group of GECO, www.geco-medical.org, 2004, 2 pp.

Shurnas, Paul S., M.D., et al., Proximal Metatarsal Opening Wedge Osteotomy: PMOW-Arthrex LPS System, Arthrex, Inc., www.arthrex.com, 2008, 1 pp.

Speed Triad Medial Technique, BioMedical Enterprises, www.bme-tx.com, 2015, 2 pp.

(56) References Cited

OTHER PUBLICATIONS

The Accu-Cut Osteotomy Guide System, BioPro Implants, www.bioproimpiants.com, Brochure No. 16932 Rev07, 2 pp.
The Accu-Cut Osteotomy Guide System, BioProimplants. www.bioproimplants.com, Brochure No. 17136, Rev4, 2 pp.
The Next Generation in Foot & Ankle Repair and Reconstruction Technology 2016, Arthrex, Inc., www.arthrex.com, 2016, 76 pp.
Weil, Lowell Jr., el al., "Anatomic Plantar Plate Repair Using the Weil Metatarsal Osteotomy Approach", Foot & Ankle Specialist, http://fas.sagepub.com/, 2011, 7 pp.

\* cited by examiner

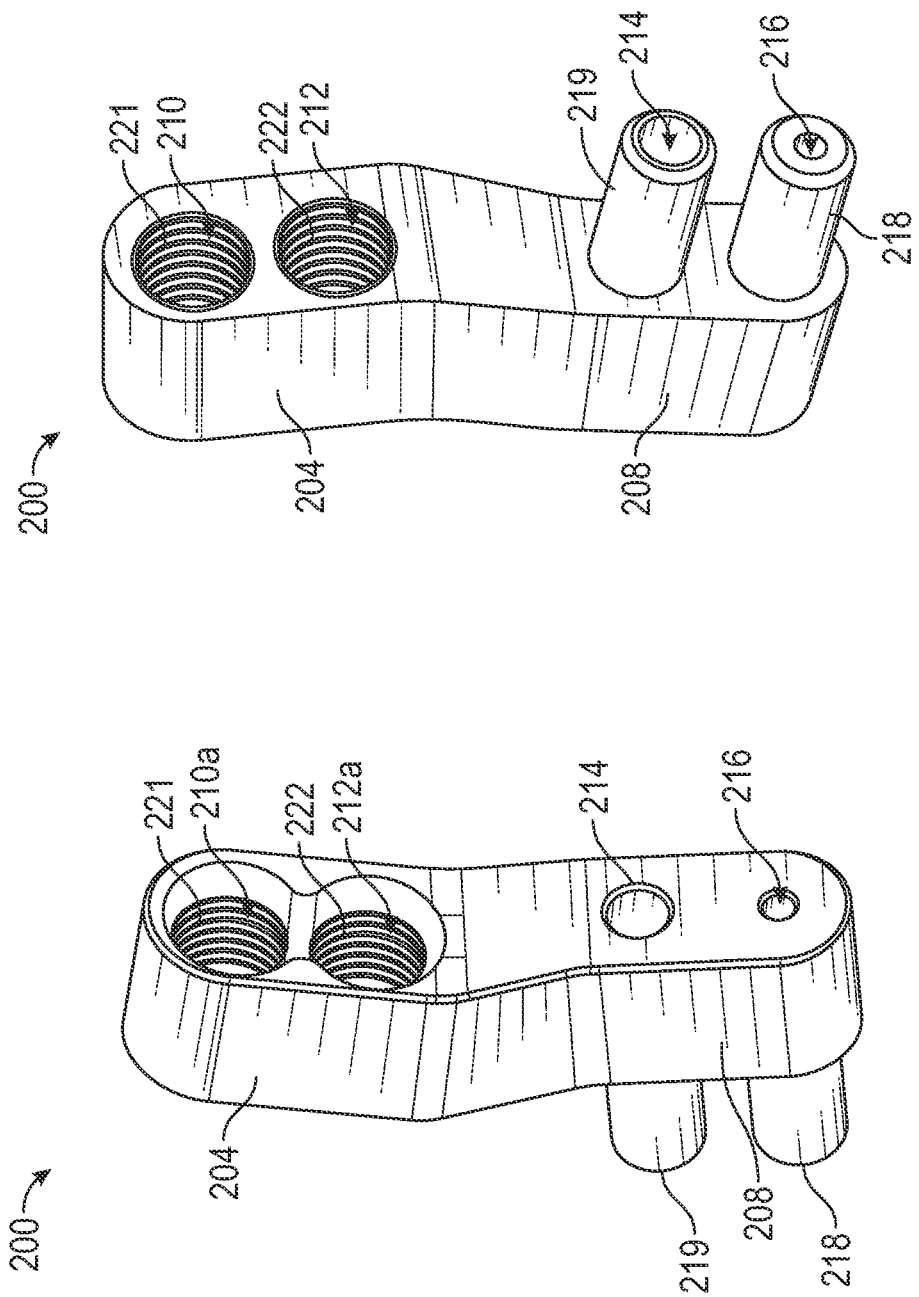

BONE REPOSITIONING GUIDE SYSTEM AND PROCEDURE

CROSS REFERENCE

This application is the national phase application of PCT Patent Application No. PCT/US2020/043525 filed Jul. 24, 2020, which claims the benefit of U.S. Patent Application No. 62/879,340 filed Jul. 26, 2019 the entirety of which is hereby incorporated by reference.

FIELD

The present invention generally relates to surgical systems and procedures for correcting alignment between two bones and a joint and particularly relates to surgical systems and procedures for correcting a bunion in a patient's foot.

BACKGROUND

Bone misalignment and/or deformation can be a source of discomfort and reduced mobility in patients, particularly in a patient's feet. One particularly common foot disorder is a bunion. Bunions are a progressive disorder, typically beginning with a leaning of the great toe. The leaning of the great toe may gradually change an angle of the bones and produce a characteristic bump on the medial side of the metatarsal near the joint of the metatarsal with the proximal phalanx. Specifically, the bunion is the prominence made of bone and at times an inflamed bursa. Hallux valgus is the condition in which the great toe deviates from the normal position toward the direction of the second toe. Accordingly, the present invention is directed to surgical systems and procedures for correction of bunions, Hallux valgus, and for bone realignments more generally.

SUMMARY

The foregoing summary is illustrative only and is not intended to be limiting. Other aspects, features, and advantages of the systems, devices, and methods and/or other subject matter described in this application will become apparent in the teachings set forth below. The summary is provided to introduce a selection of some of the concepts of this disclosure. The summary is not intended to identify key or essential features of any subject matter described herein.

According to one aspect of the disclosure, a method for correcting alignment between a first bone and a second bone by fusing a joint between the first bone and the second bone includes providing a first guide. The first guide includes a first end portion with a first cannula aligned along a first axis. A second end portion has a second cannula aligned along a second axis. The first axis is non-parallel with the second axis. The first axis is configured to intersect the first bone and the second axis is configured to intersect the second bone when the first and second bones are in a deformed configuration. A first k-wire is inserted through the first cannula and into the first bone. A second k-wire is inserted through the second cannula and into the second bone. The first guide is removed from the first and second k-wires. A second guide includes a first end portion with a first cannula. A second end portion has a second cannula. The first cannula is parallel with the second cannula. The second guide slides over the first and second k-wires. The first k-wire is received within the first cannula of the second guide and the second k-wire is received within the second cannula of the second guide. The second guide acts on the first and second k-wires to re-align the first and second bones into a corrected configuration.

In another aspect, the method includes fixing the first and second bones in the corrected configuration and removing the second guide and the first and second k-wires from the first and second bones.

In another aspect, the method includes fixing the first and second bones in the corrected configuration includes inserting a first stabilizing wire into the first and second bones.

In another aspect, the method includes attaching a first end of a bone plate with the first bone and a second end of the bone plate with the second bone such that the first and second bones are retained in the corrected configuration.

In another aspect, the method includes inserting a bone plate clip into the first and second bones.

In another aspect, the method includes resecting a first end of the first bone.

In another aspect, the first end portion of the first guide includes a third cannula aligned parallel with the first axis.

In another aspect, the method includes inserting a third k-wire into the first bone through the third cannula and resecting the first end of the first bone includes inserting a first resecting guide over the first and third k-wires to align the first resecting guide with the first end of the first bone.

In another aspect, the method includes resecting a first end of the second bone.

In another aspect, the second end of the first guide includes a fourth cannula aligned parallel with the second axis.

In another aspect, the method includes resecting the first end of the second bone.

In another aspect, the method includes inserting a second resecting guide over the second k-wire and a fourth k-wire inserted in the second bone to align the second resecting guide with the first end of the second bone.

In another aspect, the first bone is a metatarsal, the second bone is a medial cuneiform bone, the deformed configuration of the first and second bones includes a bunion and the corrected configuration of the first and second bones corrects the bunion.

In another aspect, the second guide adjusts an angle of the first bone in three orthogonal planes between the deformed configuration and the corrected configuration.

In another aspect, the second guide adjusts a position of the first bone in three orthogonal planes between the deformed configuration and the corrected configuration.

In another aspect, the method includes centering the first guide between the first bone and the second bone by inserting a centering k-wire through a centering cannula on the first guide.

In another aspect, the method includes removing the first guide from the first and second k-wires includes at least partially disassembling the first guide.

In another aspect, the method includes scanning the first bone and the second bone in the deformed configuration to render a 3D model thereof including a first virtual bone and a second virtual bone in a virtual deformed configuration, adjusting the first virtual bone and the second virtual bone in the 3D model to align the first virtual bone and the second virtual bone in a virtual corrected configuration, fixing a first virtual axis relative to the first virtual bone and fixing a second virtual axis relative to the second virtual bone in the virtual corrected configuration, the first virtual axis is parallel with the second virtual axis, and returning the first and second virtual bones to the virtual deformed configuration, the first and second virtual axes defining a correction factor therebetween in the virtual deformed configuration.

In another aspect, the method includes identifying a virtual resection plane where the first virtual bone and the second virtual bone overlap in the virtual corrected configuration, and fixing the first virtual axis relative to the first virtual bone includes aligning the first virtual axis parallel with the virtual resection plane.

In another aspect, the method includes forming the first guide based on the correction factor.

In another aspect, the correction factor includes a first virtual vector passing through a first virtual point in a virtual coordinate plane and a second virtual vector passing through a second virtual point in the virtual coordinate plane.

In another aspect, forming the first guide includes correlating the virtual coordinate plane with a coordinate plane of the first guide such that the first axis corresponds with the first virtual vector and the first virtual point and the second axis aligned corresponds with the second virtual vector and the second virtual point.

In another aspect, the each of the correction factors includes a position vector and two direction vectors corresponding to the first and second axis of the respective guides within the plurality of guides.

In another aspect, the first guide is selected from a plurality of guides, each of the plurality of guides has a different angle between the first and second axes.

According to another aspect, a method of manufacturing a kit for correcting alignment between a first bone and a second bone includes receiving a correction factor, the correction factor including a first virtual vector passing through a first virtual point in a virtual coordinate plane and a second virtual vector passing through a second virtual point in the virtual coordinate plane.

A first guide is formed based on the correction factor, the first guide including a first end portion having a first cannula aligned along a first axis and a second end portion having a second cannula aligned along a second axis. The first axis corresponds to the first virtual vector and the first virtual point and the second axis corresponds to the second virtual vector and the second virtual point, the first and second axes is non-parallel. The first guide is configured such that a first k-wire inserted through the first cannula intersects the first bone and a second k-wire inserted through the second cannula intersects the second bone in a deformed configuration.

In another aspect, the method includes receiving dimensions of a second guide, the second guide including a first end portion with a first cannula and a second end portion with a second cannula. The first cannula is parallel with the second cannula. The first guide is configured such that when sliding the second guide over the first and second k-wires, the first and second k-wires are received within the respective first and second cannula of the second guide and the second guide re-aligns the first and second bones into a corrected configuration.

In another aspect, the method includes receiving a scan of the first bone and the second bone in the deformed configuration to render a 3D model thereof including a first virtual bone and a second virtual bone in a virtual deformed configuration. The first virtual bone and the second virtual bone are adjusted in the 3D model to align the first virtual bone and the second virtual bone in a virtual corrected configuration. A first virtual axis is fixed relative to the first virtual bone and a second virtual axis is fixed relative to the second virtual bone in the virtual corrected configuration. The first virtual axis is parallel with the second virtual axis.

The first and second virtual bones are returned to the virtual deformed configuration along with the first and second virtual axes defining the first and second virtual vectors and the first and second virtual points, respectively, of the correction factor.

In another aspect, the method includes identifying a virtual resection plane where the first virtual bone and the second virtual bone overlap in the virtual corrected configuration and fixing the first virtual axis relative to the first virtual bone includes aligning the first virtual axis parallel with the virtual resection plane.

According to another aspect of the disclosure, a kit for correcting alignment between a first bone and a second bone by fusing a joint between the first bone and the second bone includes a first guide. The first guide includes a first end portion with a first cannula aligned along a first axis and a second end portion with a second cannula aligned along a second axis. The first axis is non-parallel with the second axis. The first guide is configured such that inserting a first k-wire through the first cannula intersects the first bone and inserting a second k-wire through the second cannula intersects the second bone when the first and second bones are in a deformed configuration. A second guide includes a first end portion with a first cannula and a second end portion with a second cannula. The first cannula can be parallel with the second cannula. The second guide is configured such that when the first k-wire is fixed within the first bone and the second k-wire is fixed within the second bone in the deformed configuration, sliding the second guide over first and second k-wires, with the first and second k-wires is received within the respective first and second cannula of the second guide, re-aligns the first and second bones into a corrected configuration.

In another aspect, a stabilizing wire fixes the first and second bones in the corrected configuration by insertion into the first and second bones.

In another aspect, a bone plate with a first end configured to be attached with the first bone and a second end of the bone plate configured to be attached with the second bone retains the first and second bones in the corrected configuration.

In another aspect, a bone plate clip inserts into the first and second bones in the corrected configuration.

In another aspect, a first resecting guide aligns a resecting tool with a resection location on the first bone.

In another aspect, the first resecting guide includes first and second cannula configured to be advanced over the first k-wire and a third k-wire, the third k-wire is parallel with the first k-wire.

In another aspect, a second resecting guide aligns the resecting tool with a resection location on the second bone.

According to another aspect, a method for correcting alignment between a first bone and a second bone by fusing a joint between the first bone and the second bone includes aligning a first end portion of a first guide with the first bone. The first end portion has a first cannula and a second cannula aligned in a first direction. A first k-wire is inserted through the first cannula and into the first bone and a second k-wire through the second cannula and into the first bone. A first end of the first bone is resected through a slot to form a first resected face. The slot aligns with the first end of the first bone by the first and second k-wires. A third k-wire and a fourth k-wire insert through the first guide into the second bone. A first end of the second bone is resected to form a second resected face. A second guide slides over the first, second, third and fourth k-wires to adjust a positioning of the first and second bones such that the first and second resected faces abut in a corrected configuration. The first and second bones are fixed in the corrected configuration.

In another aspect, the method includes fixing the first and second bones in the corrected configuration by inserting a stabilizing wire into the first and second bones.

In another aspect, the method includes fixing the first and second bones in the corrected configuration by attaching a first end of a bone plate with the first bone and a second end of the bone plate with the second bone such that the first and second bones are retained in the corrected configuration.

In another aspect, the method includes sliding the second guide over the first, second, third and fourth k-wires to translate the first resected face towards the second resected face.

In another aspect, the method includes sliding the second guide over the first, second, third and fourth k-wires to rotate alignment between the first bone and the second bone.

In another aspect, the third k-wire and the fourth k-wire are inserted into the second bone through a second end portion of the first guide including a third cannula and a fourth cannula. The third and fourth cannula are aligned in a second direction.

In another aspect, the first end of the second bone is resected through the slot. The slot is aligned with the first end of the second bone by the third and fourth k-wires.

In another aspect, the slot is on a resection guide including first and second apertures configured to align with the first and second k-wires.

In another aspect, the first bone is a metatarsal, the second bone is a medial cuneiform bone and the corrected configuration of the first and second bones corrects a bunion.

In another aspect, the second guide adjusts an angle of the first bone in three orthogonal planes between a deformed configuration and the corrected configuration.

In another aspect, the method includes removing the first guide from the first and second k-wires after resecting the first end of the second bone to form the second resected face.

In another aspect, the method includes removing the second guide and the first, second, third, and fourth k-wires from the first and second bones after fixing the first and second bones in the corrected configuration.

According to another aspect, a method for correcting alignment between a first bone and a second bone by fusing a joint between the first bone and the second bone includes positioning a cutting guide in a first position proximate to a first end of the first bone, the cutting guide including a cutting slot and a first and second cannula through the cutting guide. The cutting guide in the first position includes a first and second k-wire positioned through the first and second cannula and into the first bone. A first end of the first bone is resected through the cutting slot to form a first resected face. The cutting guide is removed from the first and second k-wires. The cutting guide is positioned in a second position proximate to a first end of the second bone. The cutting guide in the second position includes a third and fourth k-wires positioned through the first and second cannula and into the second bone. A first end of the second bone is resected through the cutting slot to form a second resected face. The cutting guide is removed from the third and fourth k-wires. A second guide slides over the first, second, third and fourth k-wires. The second guide adjusts a positioning of the first and second bones such that the first and second resected faces abut in a corrected configuration. The first and second bones are fixed in the corrected configuration.

In another aspect, positioning a first end portion of a first guide with the first bone, the first end portion having a third cannula and a fourth cannula, the third and fourth cannula aligned in a first direction and inserting the first k-wire through the third cannula and into the first bone and the second k-wire through the fourth cannula and into the first bone.

In another aspect, positioning a second end portion of the first guide with the second bone, the second end portion having a fifth cannula and a sixth cannula, the fifth and sixth cannula aligned in a second direction and inserting the third k-wire through the fifth cannula and into the second bone and the fourth k-wire through the sixth cannula and into the second bone.

In another aspect, fixing the first and second bones in the corrected configuration includes inserting a stabilizing wire into the first and second bones.

In another aspect, fixing the first and second bones in the corrected configuration includes attaching a first end of a bone plate with the first bone and a second end of the bone plate with the second bone such that the first and second bones are retained in the corrected configuration.

In another aspect, sliding the second guide over the first, second, third and fourth k-wires translates the first resected face towards the second resected face.

In another aspect, sliding the second guide over the first, second, third and fourth k-wires rotates the first bone relative to the second bone to adjust an alignment therebetween.

BRIEF DESCRIPTION OF THE DRAWINGS

Various examples are depicted in the accompanying drawings for illustrative purposes, and should in no way be interpreted as limiting the scope of the examples. Various features of different disclosed examples can be combined to form additional examples, which are part of this disclosure.

FIG. 2A shows a front perspective view of the alignment guide;

FIG. 2B shows a rear perspective view of the alignment guide;

DETAILED DESCRIPTION

Overview

Bunion correction or repair is a common surgery with over 100,000 surgeries performed annually in the US. Many surgical procedures for bunion repair are invasive and painful, requiring an incision of several inches and a long period of convalescence, of up to 10-12 weeks. Minimally invasive surgery has been performed in orthopedics for decades. One common procedure is known as a Lapidus bunionectomy. In a Lapidus bunionectomy, the bunion is corrected at the great toe by adjusting alignment at the first tarsometatarsal joint. The metatarsal can also be stabilized using bone screws and/or a plate to facilitate fusion between the metatarsal and the medial cuneiform bone.

However, existing Lapidus bunionectomy procedures have various drawbacks and risks. These drawbacks include requiring more than minimally invasive surgery, the use of a realignment apparatus that exhibits little control over rotation and relative angles of the metatarsal bone, procedures that rely on in-surgery trial-and-error to identify the best alignment of the patient's foot bones and in-surgery judgment to identify locations for performing resections, lack of customization to account for individual patient foot conditions, and/or a lack of usable guides for performing pre-planned resections of the foot bones. Various aspects of the bone repositioning systems and procedures described herein overcome and improve upon these existing procedures, leading to better patient outcomes.

The various features and advantages of the systems, devices, and methods for bone repositioning described herein will become more fully apparent from the following description of the examples illustrated in the figures. These examples are intended to illustrate the principles of this disclosure, and this disclosure should not be limited to merely the illustrated examples. The features of the illustrated examples can be modified, combined, removed, and/or substituted as will be apparent to those of ordinary skill in the art upon consideration of the principles disclosed herein.

Deformation Correction Procedures

Figure 1:
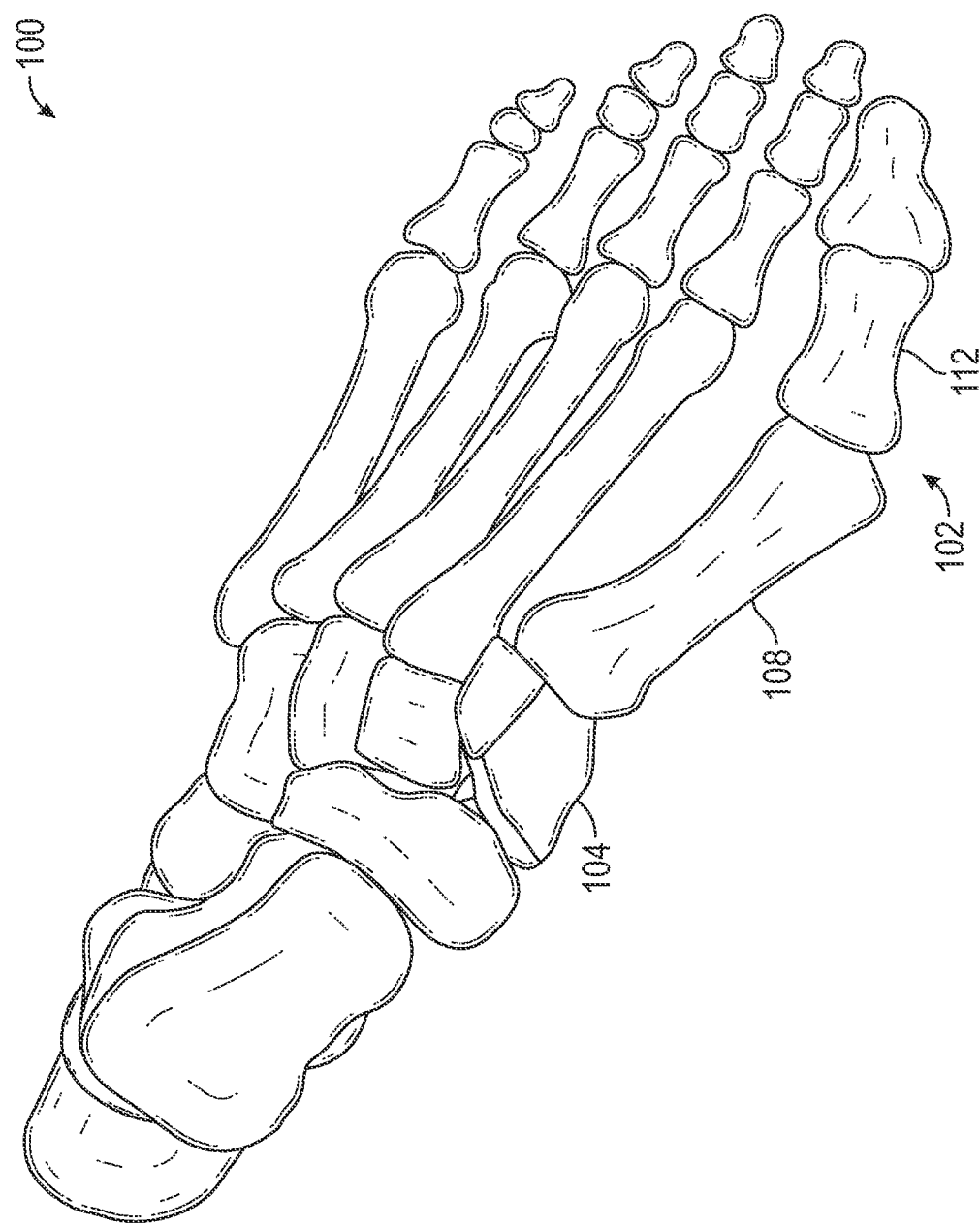
FIG. 1 shows a top view of a patient's foot in a deformed configuration.
Figure 3B:
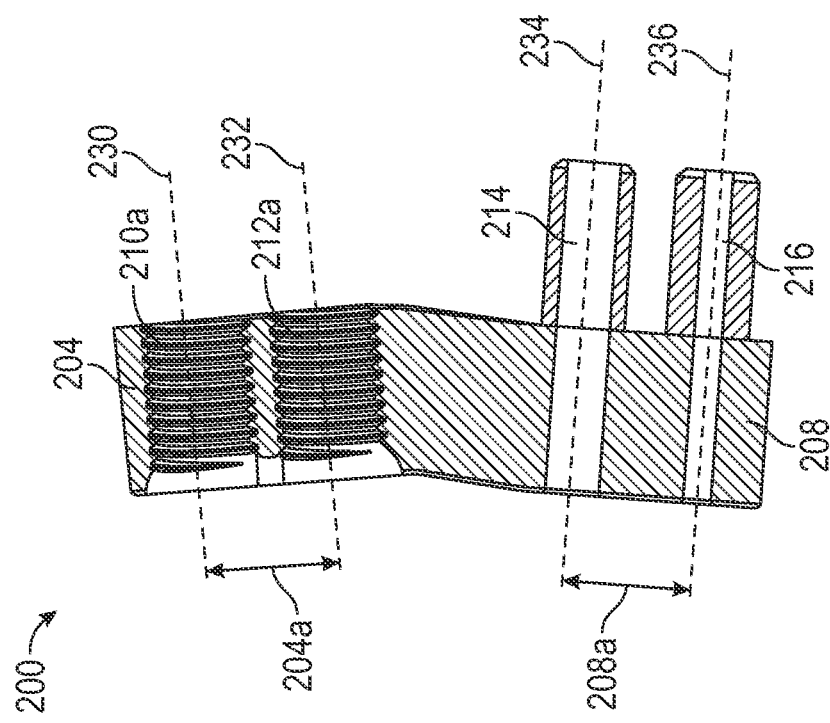
FIG. 3B shows a section view taken along the line 15B-15B in FIG. 15A.
Figure 3A:
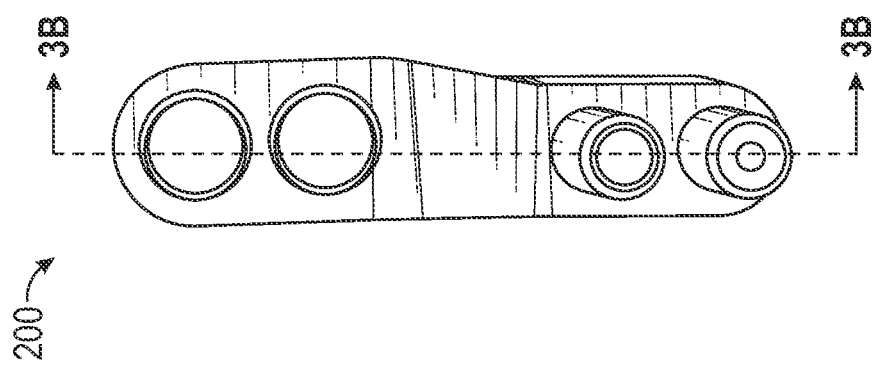
FIG. 3A shows a front view of the alignment guide.

FIG. 1 shows a skeletal view of a patient's foot 100 having one or more bones in a deformed configuration 102. The deformed configuration 102 can be a bunion, as illustrated. The deformed configuration 102 can be a misalignment between a metatarsal 108 and a phalanx 112 of the patient's great toe. The metatarsal 108 can be at an angle with respect to the phalanx at 112. A high degree of misalignment between the metatarsal 108 and the phalanx 112 can lead to severe pain and rubbing and discomfort and other problems in the patient's foot 100. Accordingly, it can be beneficial to correct the alignment between the metatarsal 108 and the phalanx 112 of the great toe.

The patient's foot 100 can further include a medial cuneiform bone 104. The medial cuneiform bone 104 can be connected with a proximal end of the metatarsal 108 (e.g., by one or more ligaments). FIGS. 1-22 illustrate systems and methods of correcting alignment between the medial cuneiform bone 104 and the metatarsal 108. In turn, proper alignment between the medial cuneiform bone 104 and the metatarsal 108 can correct alignment between the metatarsal 108 and the phalanx 112. Accordingly, the deformed configuration 102 of the patient's foot 100 can be corrected. The present disclosure relates to systems and methods for correcting the deformed configuration 102. Moreover, the systems and methods described herein can be used more generally for correcting alignment between any two bones a patient's body.

As shown in FIGS. 2A-4, the system for correcting alignment in the patient's foot 100 can include an alignment guide 200. The alignment guide 200 can be formed of a rigid material. The alignment guide 200 can include a first end portion 204. The first end portion 204 can include one or more apertures 210a, 212a. Although two apertures are described and illustrated, more or fewer apertures can be included on the first end portion 204. The apertures 210a, 212a can include internal threads 221, 222, respectively. The apertures 210a, 212a can be chamfered on one or both sides of the alignment guide 200. The apertures 210a, 212a can extend all the way through the alignment guide 200. The apertures 210a, 212a can be aligned along respective axes 230, 232. The axes 230, 232 can be parallel. Alternatively, the axes 230, 232 can be converging. The axes 230, 232 can be spaced apart a distance 204a. The distance 204a can be based on a length of the medial cuneiform bone 104.

Figure 4:
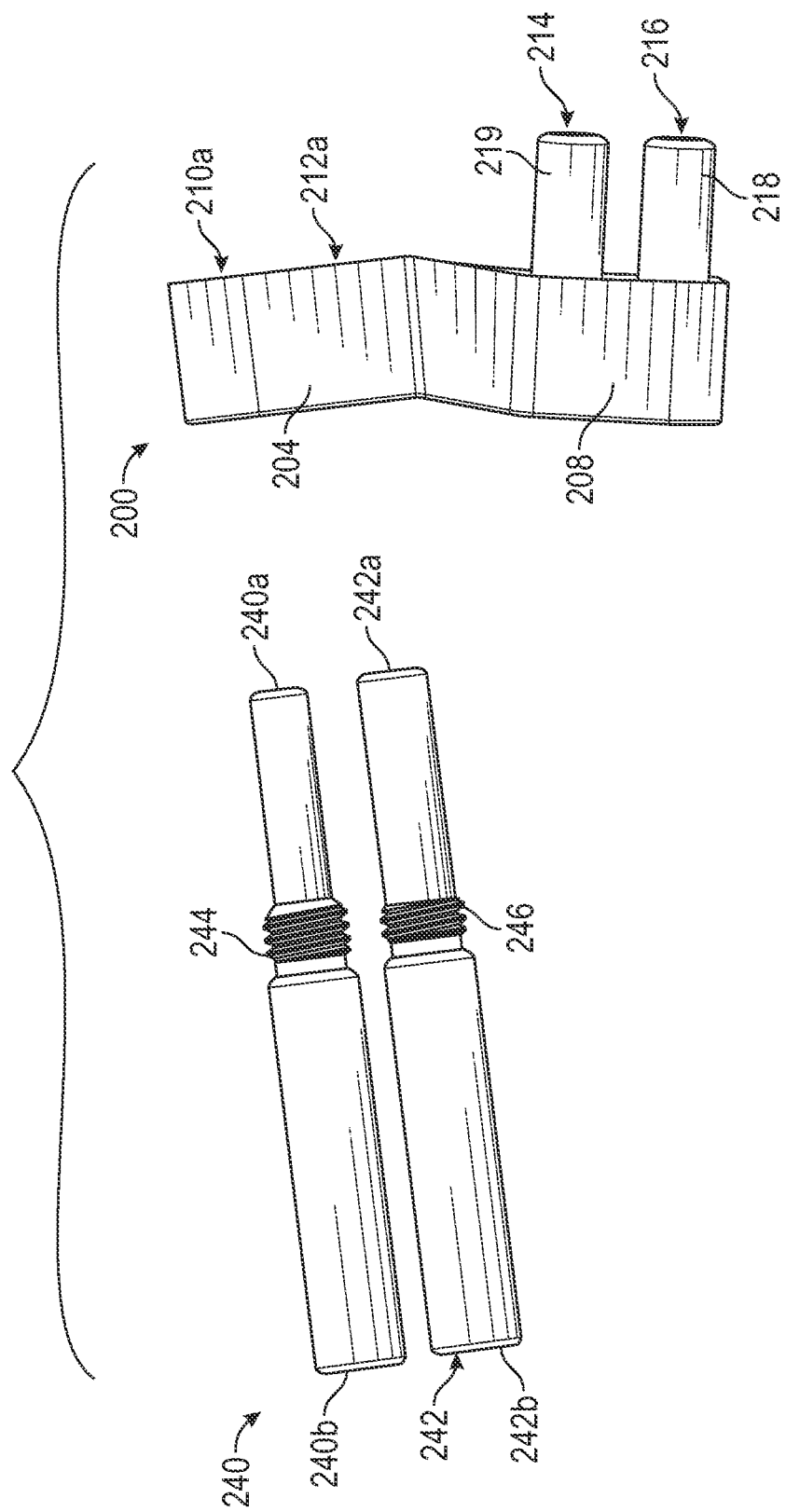
FIG. 4 shows an exploded view of the alignment guide.

As shown in FIG. 4, the alignment guide 200 can include one or more removable tubes 240, 242. The removable tubes 240 can include a first end 240a and a second end 240b. The first end 240a can be received within the aperture 210a. The removable tube 240 can include a threaded portion 244. The threaded portion 244 can engage with the internal threads 221 of the aperture 210a. The removable tubes 242 can include a first end 242a and a second end 242b. The first end 242a can be received within the aperture 212a. The removable tube 240 can include a threaded portion 246. The threaded portion 246 can engage with the internal threads 222 of the aperture 212a.

The removable tube 240 can define a cannula 210. When installed within the aperture 210a, the cannula 210 can be aligned along the axis 230 of the aperture 210a. The removable tube 242 can define a cannula 212. When installed within the aperture 212a, the cannula 212 can be aligned along the axis 232 of the aperture 212a. The cannula 210, 212 can define different diameters therethrough. The cannula 212 can have a greater diameter than the cannula 210 (or vice-versa). In other implementations, the cannula 210, 212 can define the same different diameters therethrough. In other implementations, the cannula 210, 212 can define varying diameters therethrough.

The alignment guide 200 can include a second end portion 208. The second end position 208 can include one or more cannula 214, 216. The cannula 214, 216 can be defined through a body of the alignment guide 200 and/or through respect extensions 219, 218 thereof. Although two cannula are described and illustrated, more or fewer cannula can be included on the second end portion 208. Moreover, the second end portion 208 can include removable inserts or removable portions (e.g., removable tubes) around the cannula 214, 216.

The cannula 214, 216 can extend all the way through the alignment guide 200 (e.g., including the extensions 218, 219). The cannula 214, 216 can define different diameters therethrough. The cannula 214 can have a greater diameter than the cannula 216 (or vice-versa). In other implementations, the cannula 214, 216 can define the same different diameters therethrough. In other implementations, the cannula 214, 216 can define varying diameters therethrough.

The cannula 214, 216 can be aligned along respective parallel axes 234, 236. The axes 234, 236 can be spaced apart a distance 208a. The distance 204a can be based on a length of the metatarsal bone 108.

Figure 5:
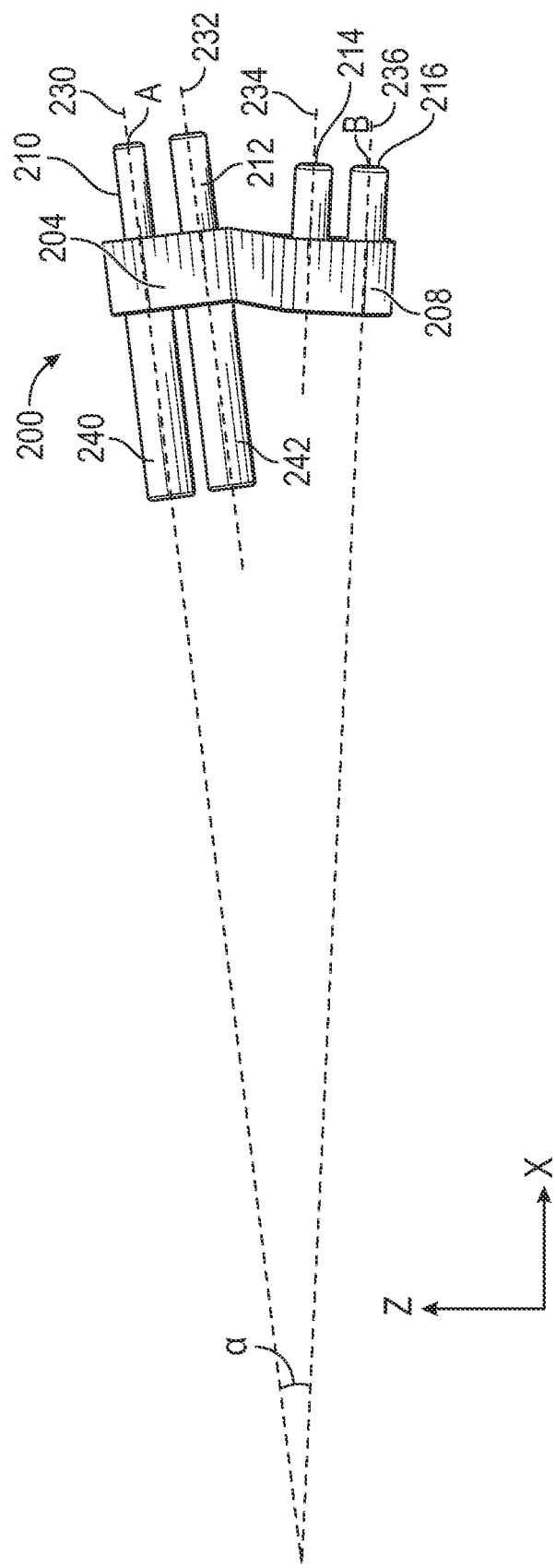
FIG. 5 shows an angle between cannula of the alignment guide.
Figure 6:
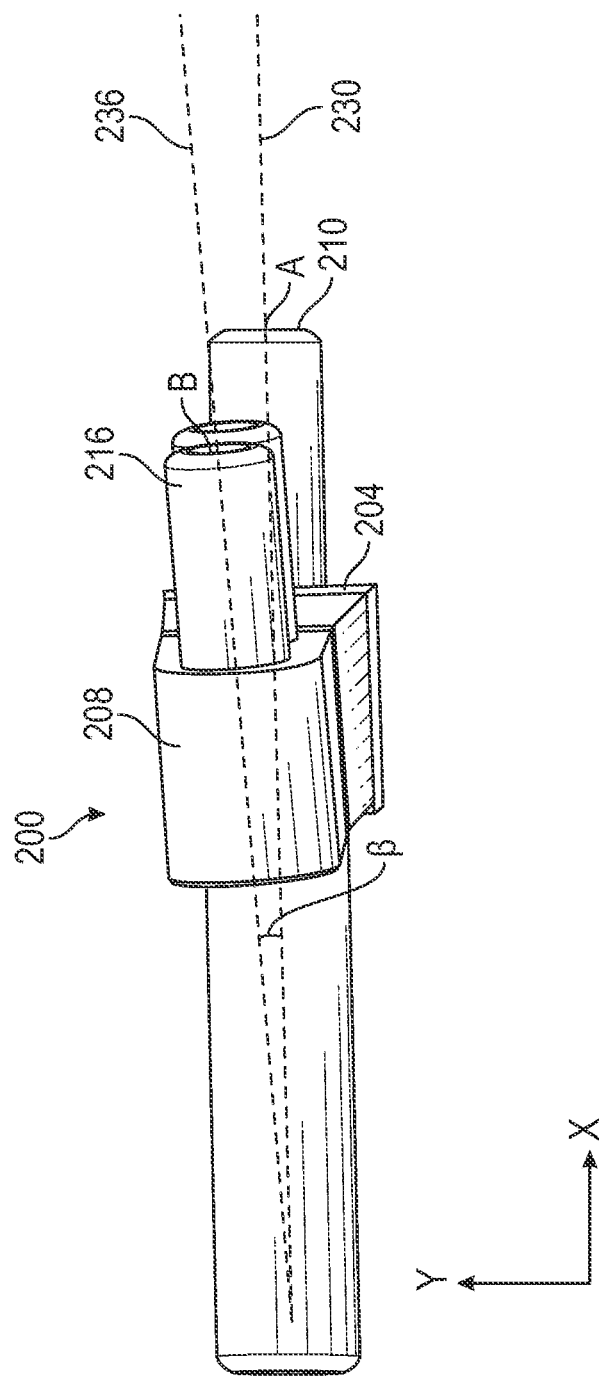
FIG. 6 shows a second angle between cannula of the alignment guide.
Figure 7:
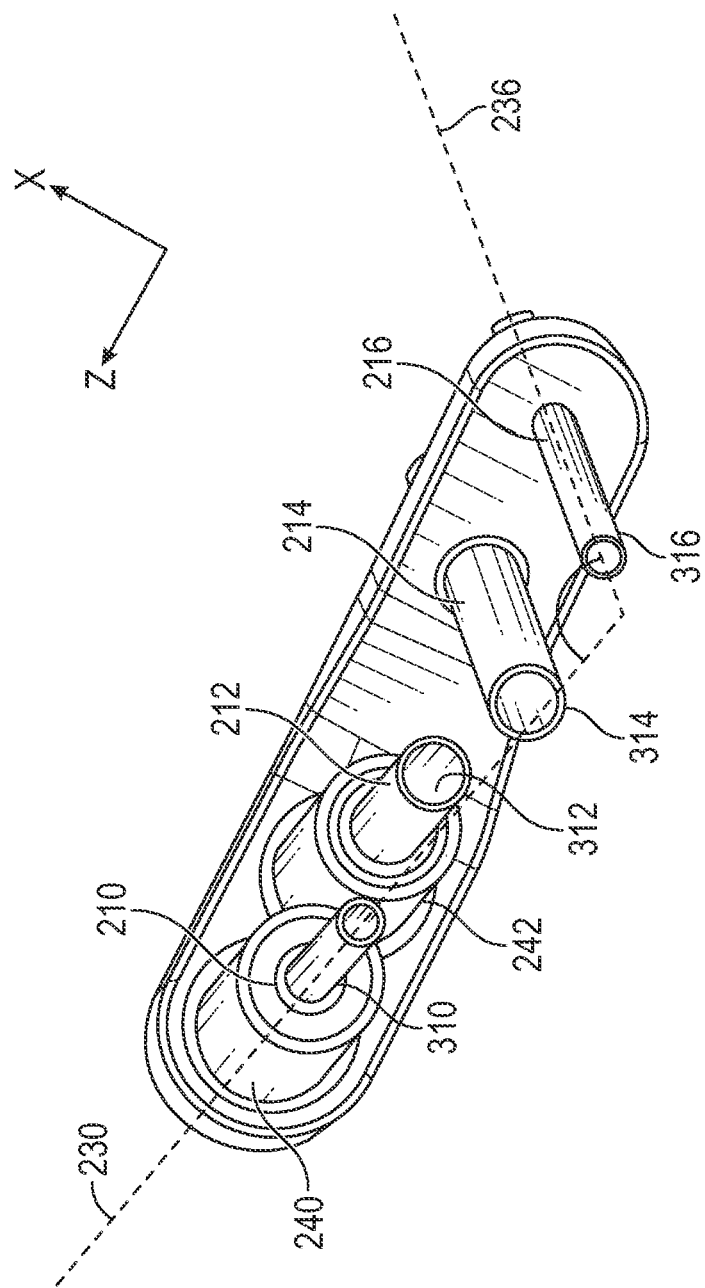
FIG. 7 shows a third angle between cannula of the alignment guide.

FIGS. 5-7 shows the assembled alignment guide 200. The first end portion 204 can define a positioning and orientation of a first set of cannula (e.g., cannula 210, 212). The second end portion 208 can define a positioning and orientation of a second set of cannula (e.g., cannula 214, 216). The first set of cannula and the second set of cannula can be offset from each other and/or angled with respect to each other.

FIG. 5 shows an angle α between the axis 230 of the cannula 210 and the axis 236 of the cannula 216. The angle α defines the relative orientation angle between the first set of cannula on the first end 204 and the second set of cannula on the second end 208. The angle α can be defined in an z-x plane in a Cartesian coordinate system (having x, y, and z axes). The cannula 210 can include a point A. Alternatively, the point A can be any fixed position along the cannula 210. The point A can have an x, y, and z coordinate location in a Cartesian coordinate system (having x, y, and z axes). The cannula 216 can include a point B. Alternatively, the point B can be any fixed position along the cannula 216. The point B can have an x, y, and z coordinate location in the Cartesian coordinate system. The points A and B can define a relative position of the axes 230, 236 in the Cartesian coordinate system.

FIG. 6 shows an angle β between the axis 230 of the cannula 210 and the axis 236 of the cannula 216. The angle β defines the relative orientation angle between the first set of cannula on the first end 204 and the second set of cannula on the second end 208 in a y-x plane. FIG. 7 shows an angle γ between the axis 230 of the cannula 210 and the axis 236 of the cannula 216. The angle γ defines the relative orientation angle between the first set of cannula on the first end 204 and the second set of cannula on the second end 208 in a y-z plane.

Together, the relative positions of the points A and B and at least two of the relative angles α, β, and γ can define the axis of the cannula on the alignment guide 200. Using the proper selection of the relative angles α, β, and/or γ, and/or the relative positions of the points A, B, the alignment guide 200 can be used to correctly align the bones in the patient's foot 100, as described further below.

Figure 8:
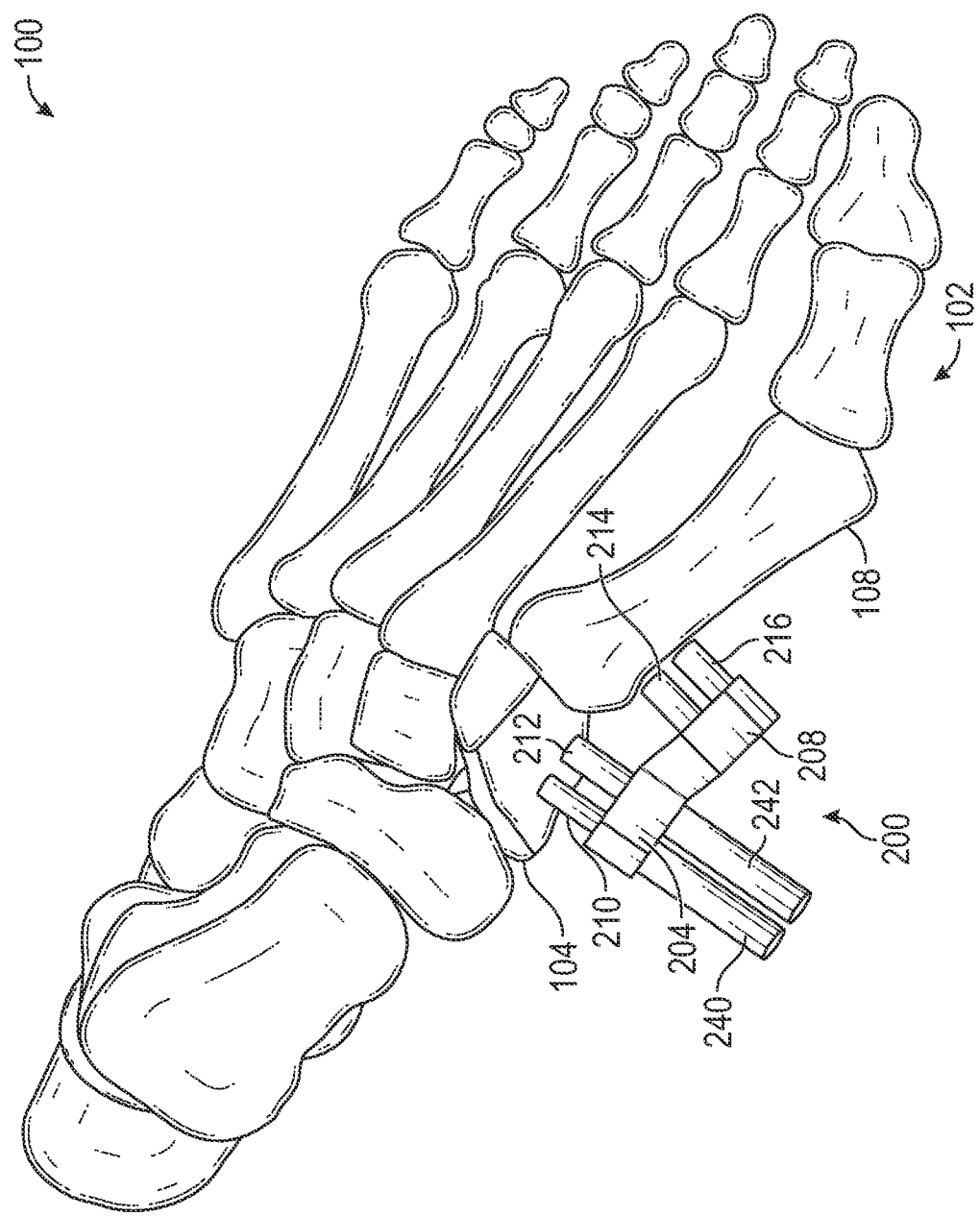
FIG. 8 shows an alignment guide aligned with a medial cuneiform bone and a metatarsal bone in the patient's foot.
Figure 9:
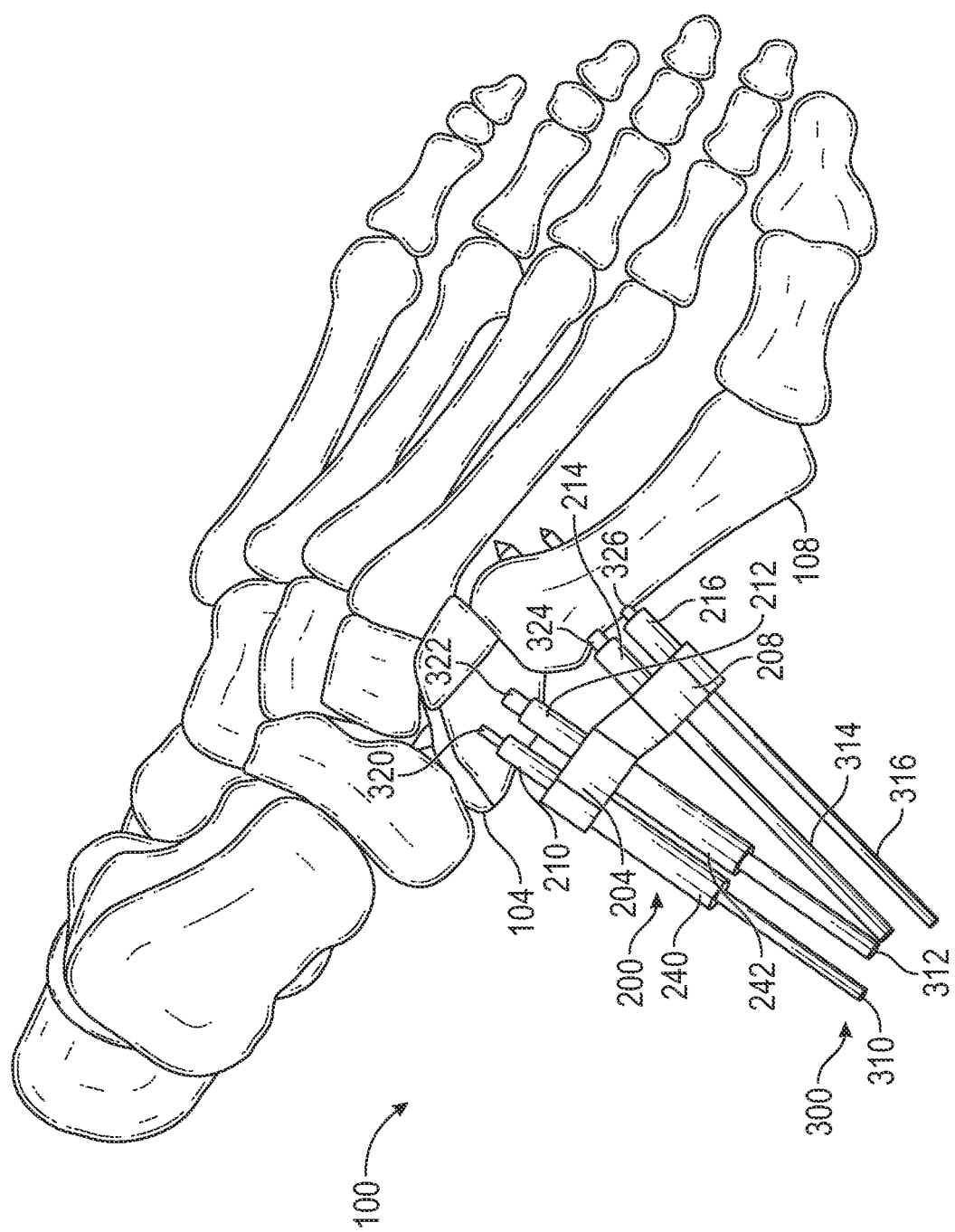
FIG. 9 shows insertion of a plurality of k-wires into the medial cuneiform bone and the metatarsal bone through the alignment guide.

As shown in FIG. 8, the alignment guide 200 can be aligned with the patient's foot 100. The first end portion 204 can be generally aligned with the medial cuneiform bone 104. The second end portion 208 can be generally aligned with the metatarsal 108. As shown in FIG. 9, a plurality of k-wire 300 can be extended through respective cannula of the alignment guide 200. The k-wires can extend through the cannula and into the respective medial cuneiform 104 and the metatarsal bone 108. A first k-wire 310 can be inserted through the cannula 210 and into the medial cuneiform 104. The first k-wire 310 can be inserted at an insertion point 320 on the medial cuneiform bone 104. A second k-wire 312 can be inserted through the cannula 212. The second k-wire 312 can be inserted through the medial cuneiform bone 104 at an insertion point 322. A third k-wire 314 can be inserted through the cannula 214. The third k-wire 314 can intersect and be inserted into the metatarsal 108 at an insertion point 324. A fourth k-wire 316 can be inserted through the fourth cannula 216. The fourth k-wire 316 can be inserted into the metatarsal 108 at an insertion point 326.

The first and second k-wires 310, 312 can be parallel with each other, based on the parallel cannula 210, 212. The third and fourth k-wires 314, 316 can be parallel with each other, based on the cannula 214, 216. One or more of the insertion points 320, 322, 324, 326 (e.g., at least one on each bone 104, 108) can be in predetermined locations on the patient's foot. The lengths of the extensions 218, 219 and/or the tubes 240, 242 can provide greater stability to the k-wires 300 that are received therein. Diameters of the k-wires 300 can be sized according the diameters of the respective cannula of the alignment guide 200 to ensure accurate insertion at angles into the bone 104, 108. Moreover, the k-wires 300 can be matched to the correct cannula based on different diameter sizes.

Figure 10:
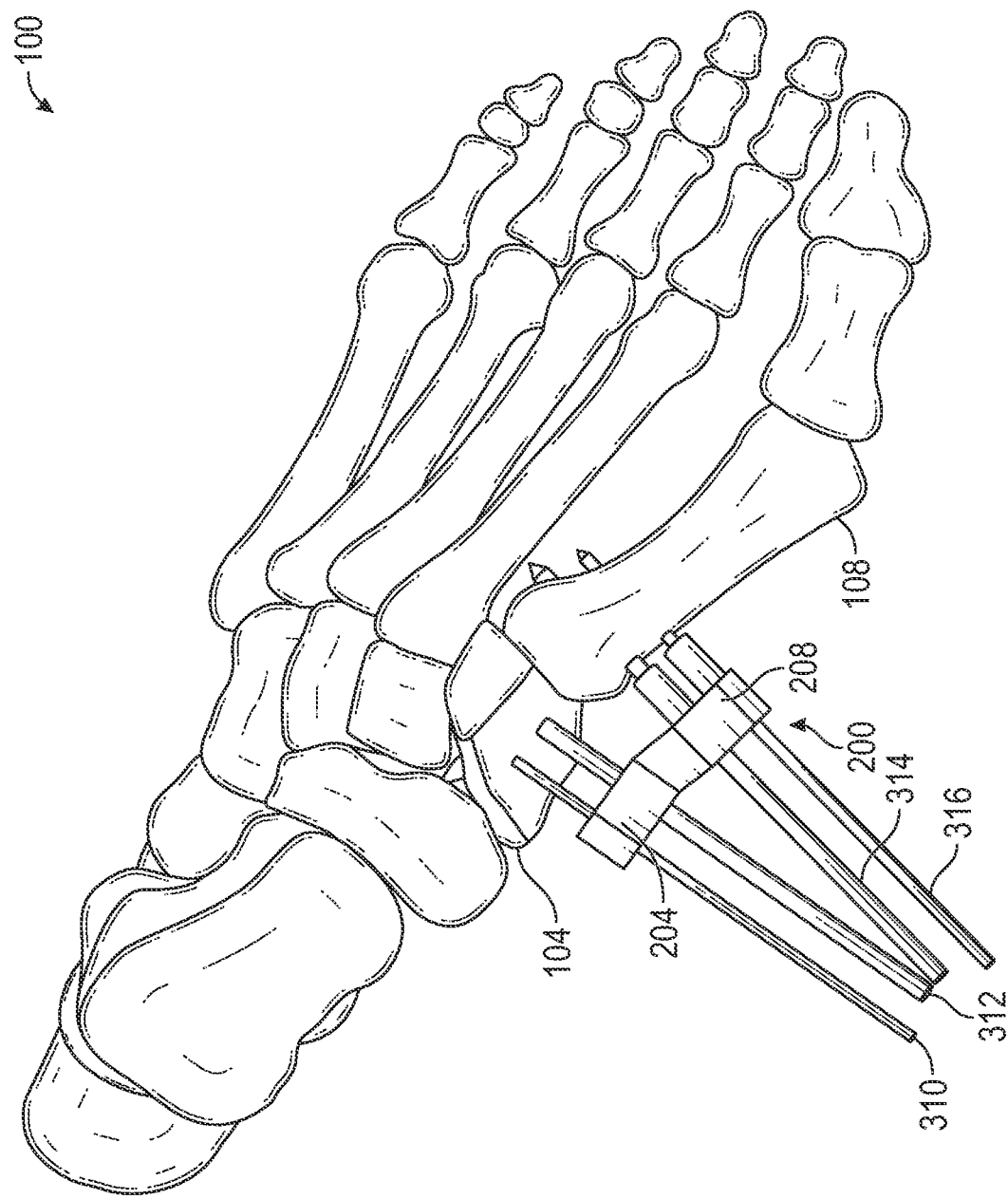
FIG. 10 shows a partial disassembly of the alignment guide.

FIG. 10 shows removal of the tubes 240, 242 from the first end 204 of the alignment guide 200. The first and second tubes 240, 242 are removed from the first end portion 204 to enable the alignment guide 200 to be removed from the plurality of k-wires 300 inserted within the medial cuneiform bone and metatarsal bone 108. In certain circumstances, without a removable or otherwise deconstructable element, it can be difficult for a user to remove the alignment guide 200 from the plurality of k-wires 300 because of the misalignment between the first and second ends 204, 208.

Figure 11A:
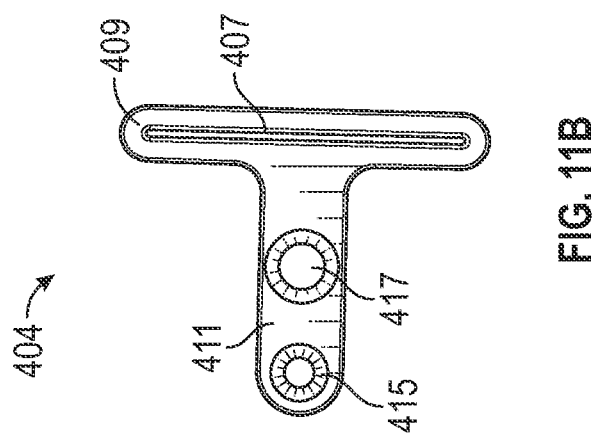
FIG. 11A shows a perspective view of a resection guide.
Figure 11B:
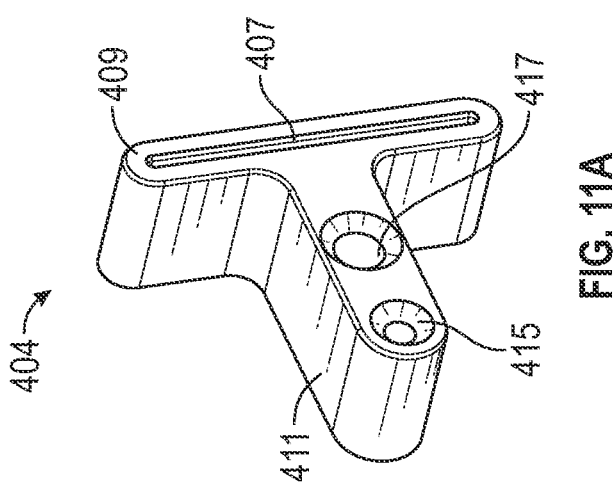
FIG. 11B shows a front view of the resection guide.

As shown in FIGS. 11A-B, the system for correcting alignment in the patient's foot 100 can include a resection guide 404. The resection guide 404 can align a resecting tool (not shown), such as a saw, a broach or the like, with an end of the medial cuneiform bone 104 and/or an end of the metatarsal bone 108, respectively.

The resection guide 404 can include a cannulated portion 411. The cannulated portion 411 can include one or more apertures 415, 417. The resection guide 404 can include a plane portion 409. The plane portion can include a slot 407 for aligning the resecting tool. The apertures 415, 417 can interact with one or more k-wires (e.g., k-wires 300) or pins to align the plane portion 409 with the desired target location for the resection tool.

The plane portion 409 (e.g., a plane defining the slot 407) can be generally perpendicular with the cannulated portion 411 (e.g., an axis between the apertures 415, 417). In other implementations, the plane portion 409 can be angled with respect to the cannulated portion 411.

The apertures 415, 417 can extend through the cannulated portion 411. The apertures 415, 417 can be sized to align with the k-wires or pins. The slot 407 can extend through the plane portion 409. The slot 407 can have a height and thickness sized to accommodate the cutting portion of the resection tool. The slot 407 can have a depth sufficient to maintain alignment of the resection tool with the desired target location.

Depending on a planned corrected configuration of the first cuneiform bone 104 with the metatarsal 108, it may be necessary to remove material from one or both inner ends of the cuneiform bone 104 and the metatarsal 108. The angle between the cuneiform bone 104 and the metatarsal 108 can be adjusted in the corrected configuration. The lengths of one or both of the cuneiform bone 104 and the metatarsal 108 can also be adjusted in the corrected configuration. Each of these adjustments can contribute to the correction of the deformity in the patient's foot 100.

Figure 12A:
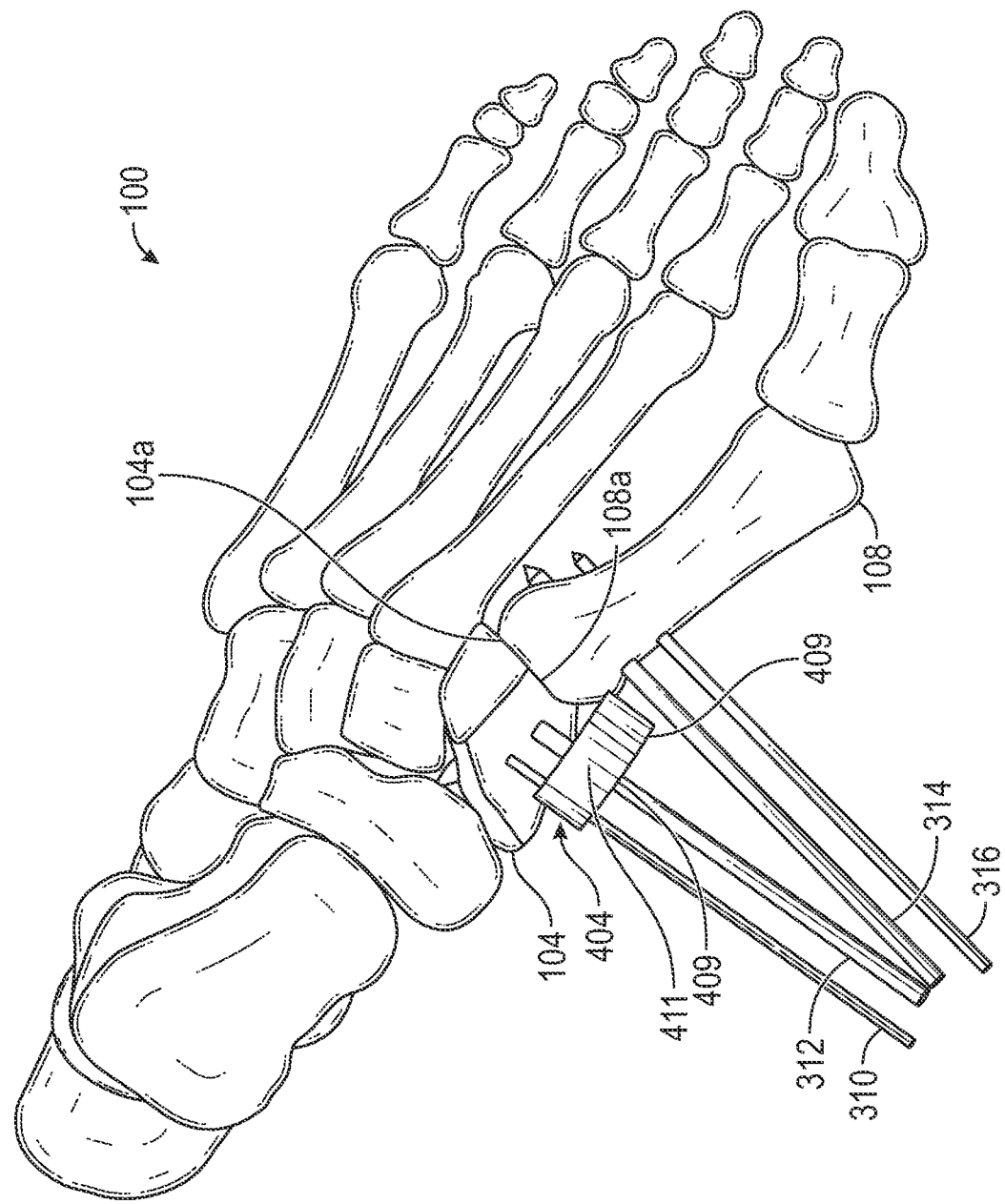
FIGS. 12A-B shows the alignment guide removed and the installation of a first resection guide.
Figure 12B:
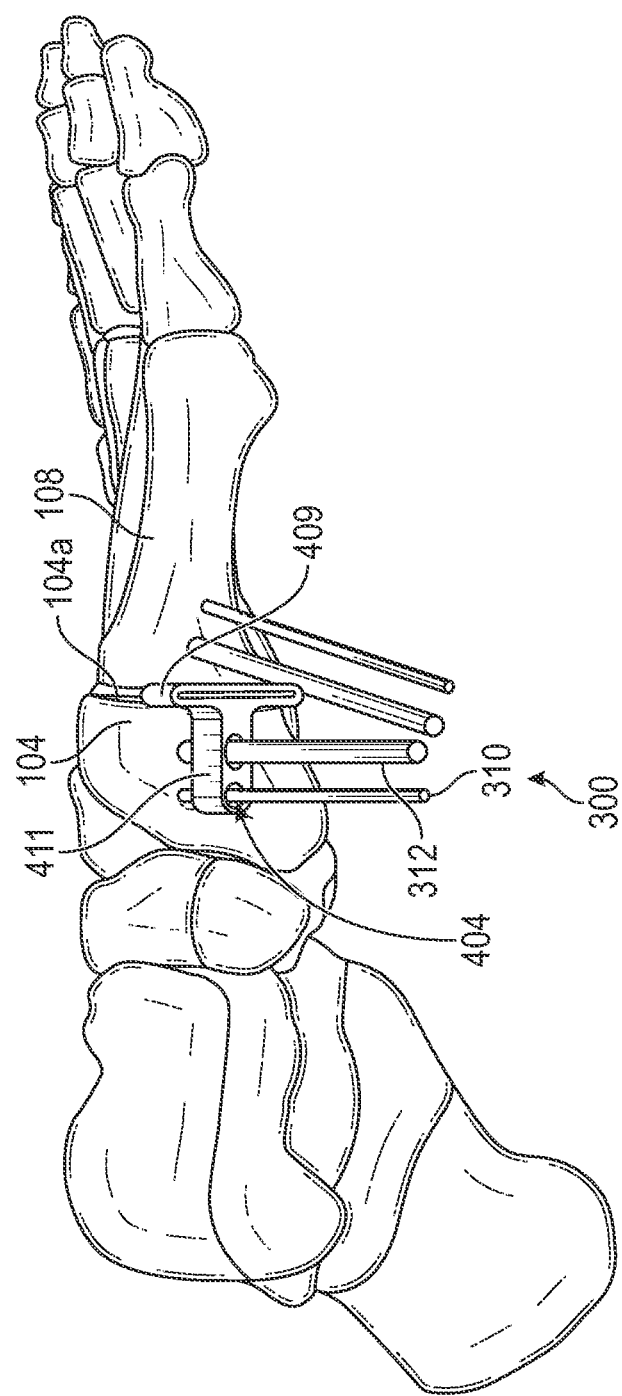

Accordingly, FIGS. 12A-B show usage of the first resection guide 404 to align a resection tool with a first inner end of the first cuneiform bone 104. The cannulated portion 411 can be received over the first and second k-wire 310, 312 on the apertures 415, 417, respectively. This can align the plane portion (e.g., the slot 407) with the end of the first cuneiform bone 104. A resection plane 104a can be cut into the first cuneiform bone 104 using a resecting tool through the slot 407. The resection plane 104a can be aligned with the first and second k-wire 310, 312.

Figure 13:
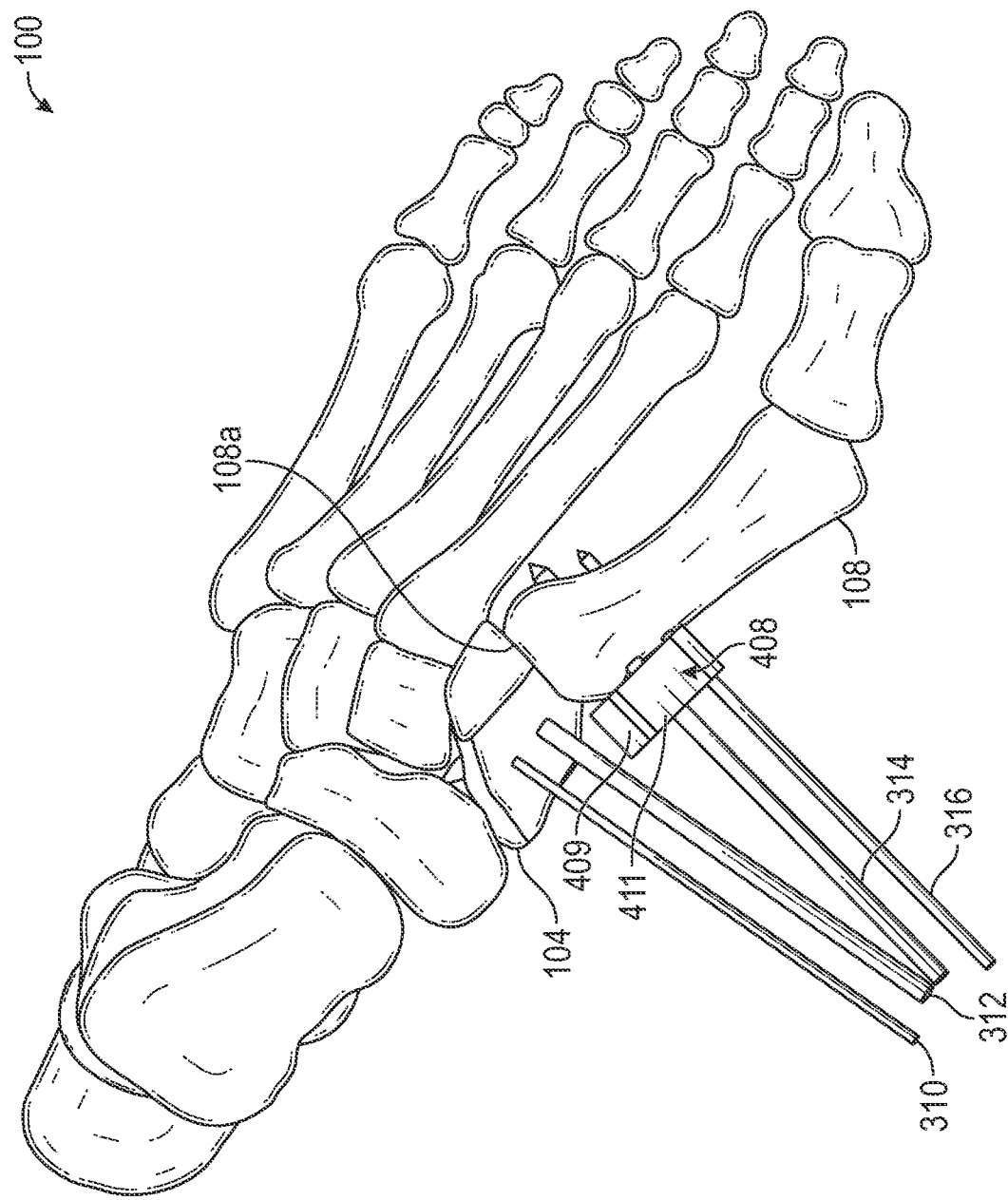
FIG. 13 shows the installation of a second resection guide.

FIG. 13 shows usage of a second resection guide 408 to align a resection tool with a first inner end of the metatarsal bone 108. The second resection guide 408 can include the same components as the resection guide 404 (e.g., a plane portion 409 and a cannulated portion 411).

The cannulated portion 411 of the second resection guide 408 can be received over the third and fourth k-wires 314, 316 on apertures 415, 417, respectively. The third and fourth k-wires can align the plane portion 409 and a slot 407 with the end of the metatarsal bone 108. A resection plane 108a can be cut into the metatarsal bone 108 using a resecting tool through the slot 407. The resection plane 108a can be aligned with the third and fourth k-wires 314, 316. In some implementations, the resection guide 404 can be used to form the resection plane 108a instead of the section resection guide 408.

Figure 14A:
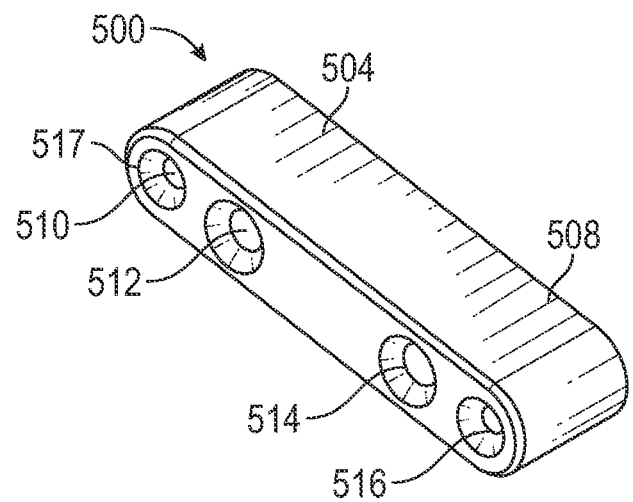
FIG. 14A shows a perspective view of the correction guide.
Figure 14B:
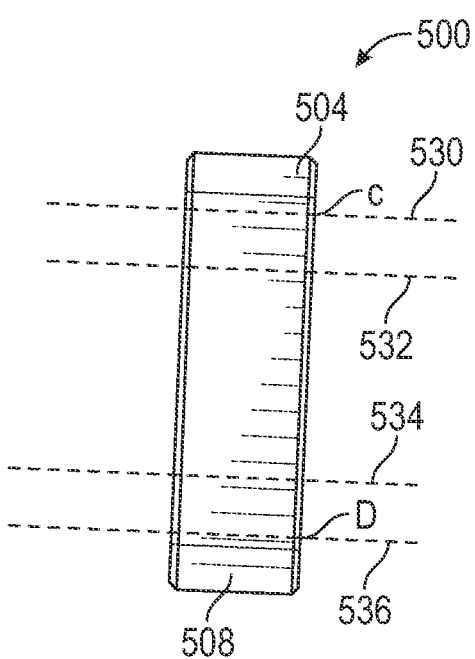
FIG. 14B shows a top view of the correction guide.
Figure 15A:
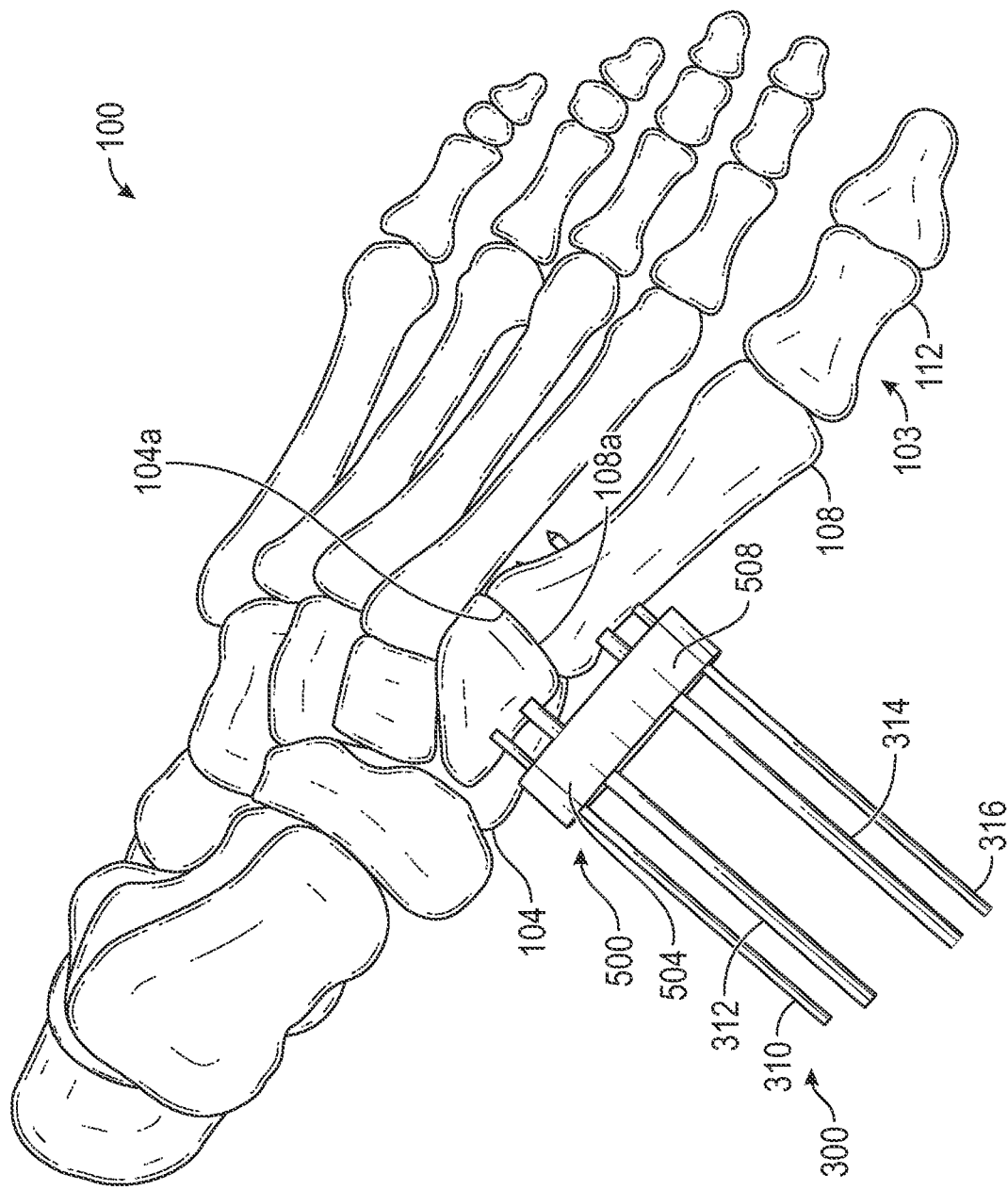
FIGS. 15A-B shows a correction guide assembled over the plurality of k-wires to align the medial cuneiform bone and the metatarsal bone of the patient's foot into a corrected configuration.
Figure 15B:
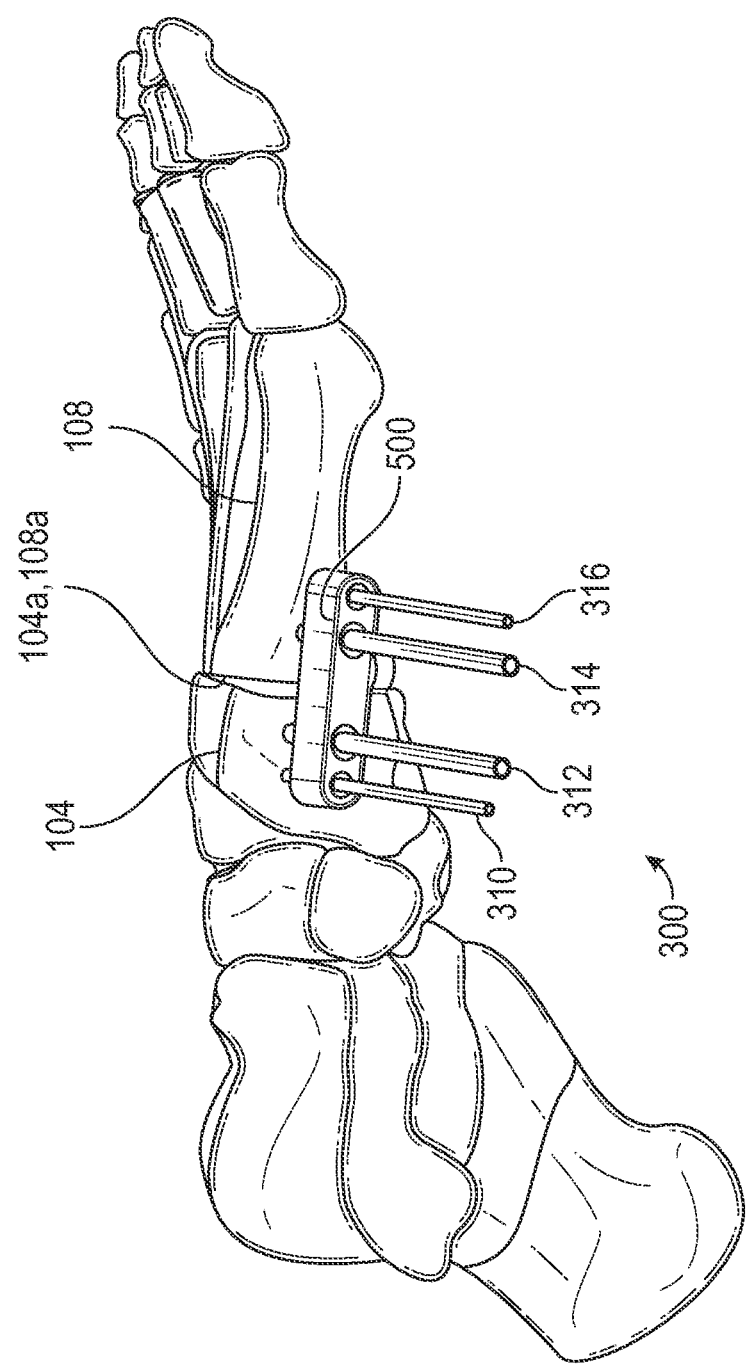

As shown in FIGS. 14A-B, the system for correcting alignment in the patient's foot 100 can include a correction guide 500. The correction guide 500 can align the bones in the patient's foot 100 into a corrected configuration 103, as shown in FIG. 15. The correction guide 500 can include a first end portion 504. The first end portion 504 can include one or more cannula 510, 512. The cannula 510, 512 can extend through the correction guide 500. The cannula 510, 512 can correspond to the first and second k-wires 310, 312, respectively inserted within the medial cuneiform bone 104. The cannula 510, 512 can be aligned along first and second axes 530, 532, respectively. The first and second axes 530, 532 can be parallel.

The correction guide 500 can include a second end portion 508. The second end portion 508 can include one or more cannula 514, 516. The cannula 514, 516 can extend through the correction guide 500. The cannula 514, 516 can correspond to the third and fourth k-wires 314, 362, respectively inserted within the metatarsal bone 108. The cannula 514, 516 can be aligned along third and fourth axes 534, 536, respectively. The third and fourth axes 534, 536 can be parallel.

The first and second axes 530, 532 can be parallel with the third and fourth axis 534, 536. The first and second axes 530, 532 can aligned within the same plane as the third and fourth axis 534, 536. In other implementations, the first and second axes 530, 532 can be aligned out of plane with (e.g., offset from) the third and fourth axis 534, 536.

The first axis 530 can extend through a point C. The point C can have a position (x, y, z) in the Cartesian coordinate plane. The fourth axis 536 can extend through a point D. The point D can have a position (x, y, z) in the Cartesian coordinate plane. The points C and D can define a relative position of the first and fourth axes 530, 536 in the Cartesian coordinate system.

As shown in FIG. 15, the correction guide 500 can be received on the k-wires 300. The first and second k-wires 310, 312 can be received within the cannula 510, 512, respectively, on the first end 504 of the correction guide 500. The third and fourth k-wires 314, 316 can be received within the cannula 514, 516, respectively, on the second end 508 of the correction guide 500.

Accordingly, the correction guide 500 can align the metatarsal bone 108 relative to the medial cuneiform bone 104 as it is advances on the k-wires 300. The correction guide can orient the metatarsal bone 108 and the proximal phalanx 112 into the corrected configuration 103. Re-orientation of the metatarsal 108 relative to the medial cuneiform bone 104 can include rotation and/or translation of the metatarsal 108 in the Cartesian coordinate system (e.g., in three orthogonal planes). The degree of rotation and/or translation of the metatarsal 108 can be determined based on the angles α, β, and/or γ, and/or any differences in the relative positions of the axes between the alignment guide 200 and the correction guide 500 (e.g., any differences in the relative positions defined by points A, B and points C, D).

The corrected configuration 103 can include one or more corrections to the alignment of the bones of the patient's foot 100. For example, the metatarsal 108 can be generally aligned with the proximal phalanx 112 of the great toe. The corrected configuration 103 can promote healing of the bunion and/or *hallux valgus* deformity. The resected face 104a of the medial cuneiform bone 104 can be abutted against the resected face 108a of the metatarsal bone 108. This abutment can promote the union or fusion of the metatarsal 108 with the medial cuneiform bone 104. Proper abutment can require translation of the metatarsal 108 relative to the medial cuneiform bone 104.

Figure 16:
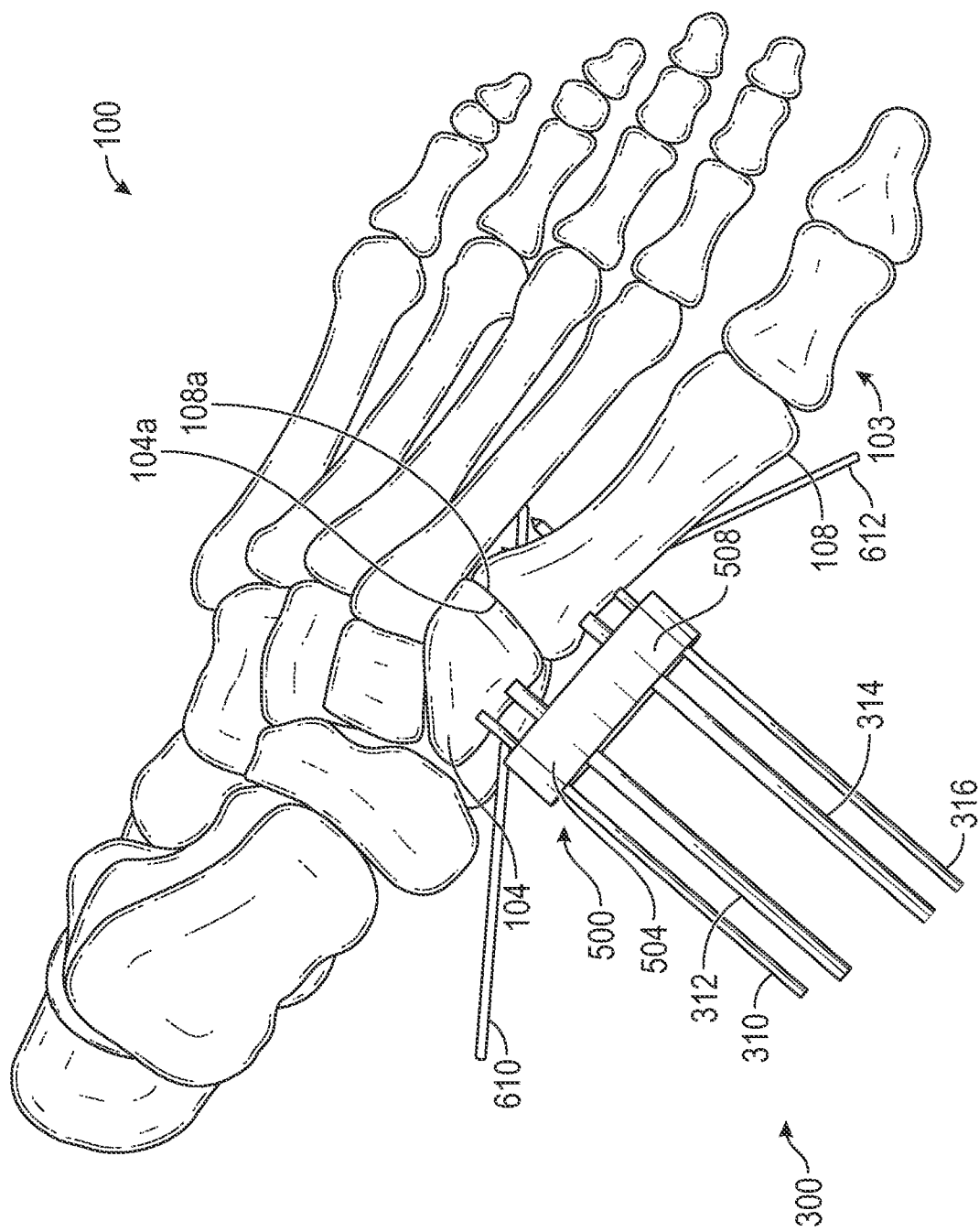
FIG. 16 shows the insertion of first and second fixing k-wires into the medial cuneiform bone and the metatarsal bone.

As shown in FIG. 16, the medial cuneiform bone 104 can be fixed temporarily or permanently relative to the metatarsal 108 in the corrected configuration 103. A first fixing k-wire 610 can be inserted into the medial cuneiform bone 104 and the metatarsal bone 108. The first fixing wire 610 can extend through the resection faces 104a, 108a. A second fixing k-wire 612 can be inserted through the metatarsal 108 and into the medial cuneiform bone 104. The second fixing k-wire 612 can be inserted through the resection planes 104a, 108a. In other implementations, any temporary or permanent fixing means can be used for connecting the medial cuneiform bone 104 with the metatarsal bone 108 in the corrected configuration. For example, the medial cuneiform bone 104 and the metatarsal bone 108 can be screwed together, braced together, adhered together or otherwise connected together on a temporary or permanent basis.

Figure 17:
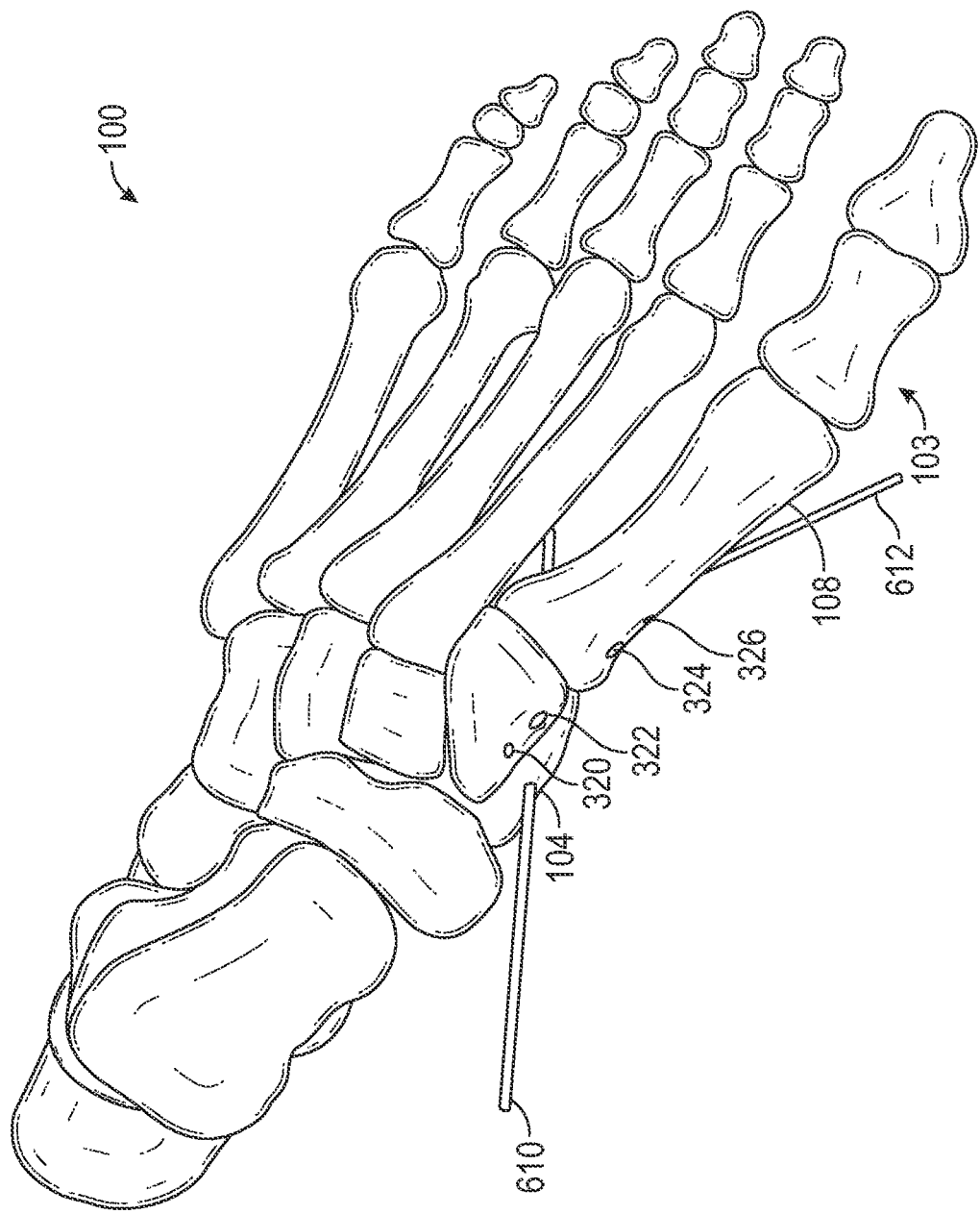
FIG. 17 shows the patient's foot with the plurality of k-wires removed.

As shown in FIG. 17, with the medial cuneiform bone 104 and the metatarsal bone 108 fixed in the corrected configuration 103, the correction guide 500 can be removed from the plurality of the k-wires 300. The plurality of k-wires 300 can be removed from the medial cuneiform bone 104 and/or the metatarsal bone 108.

Figure 18:
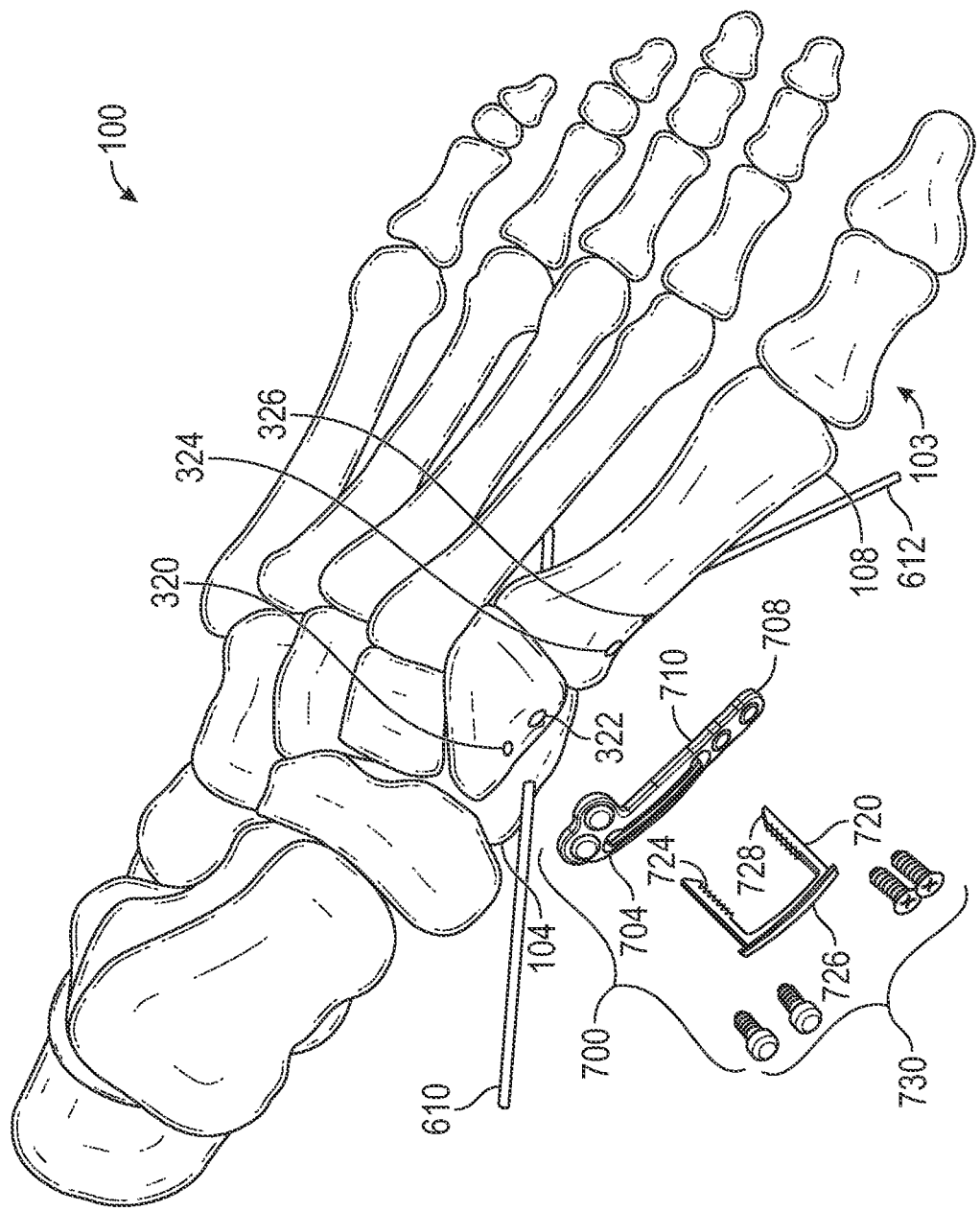
FIG. 18 shows an exploded view of a bone plate assembly aligned with the medial cuneiform bone and the metatarsal bone in the corrected configuration.
Figure 21:
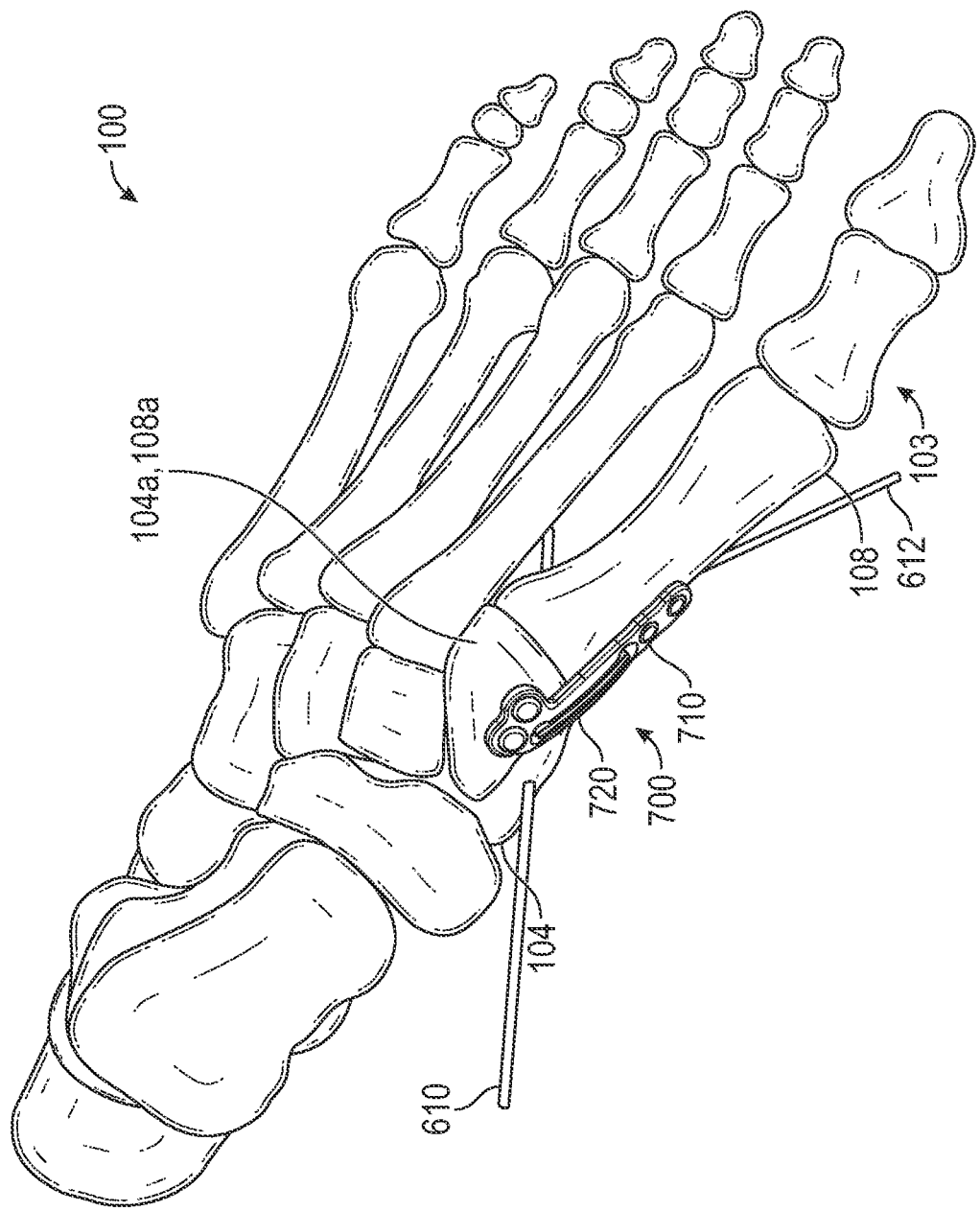
FIG. 21 shows the bone plate assembly assembled with the medial cuneiform bone and metatarsal bone in the corrected configuration.
Figure 22:
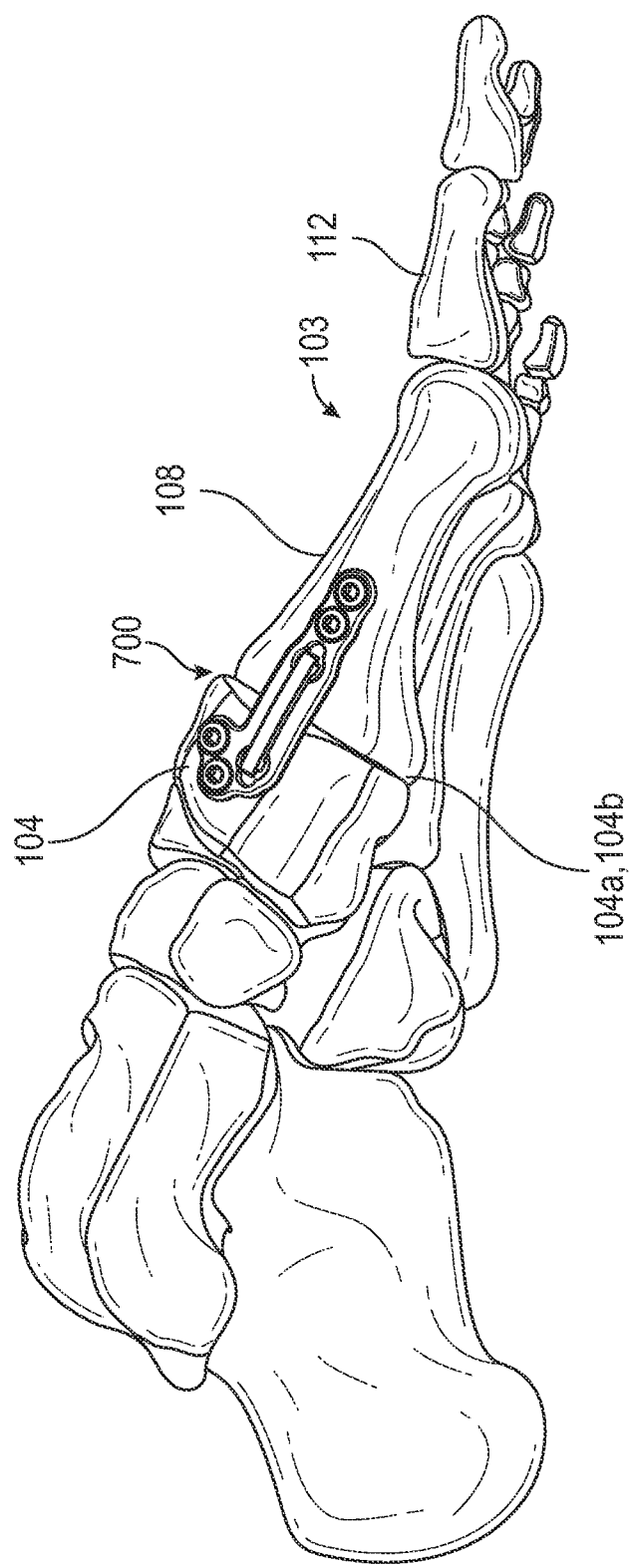
FIG. 22 shows a side view of the patient's foot in the corrected configuration.

As shown in FIG. 18, the system for correcting alignment in the patient's foot 100 can include a bone plate assembly 700. The bone plate assembly 700 attach the medial cuneiform bone 104 and the metatarsal 108, as shown in FIGS. 21-22. The bone plate assembly 700 can include a bone plate 710. The bone plate 710 can include a first end 704 and a second end 708. The bone plate assembly 700 can include a bone clip 720. The bone clip 720 can couple between the medial cuneiform bone 104 and the metatarsal bone 108. The bone clip 720 can include a first prong 724 and second prong 728 connected by a transverse member 726. The bone plate assembly 700 can include a plurality of fasteners 730 such as bone screws, pins or other fasteners known in the field of orthopedics.

Figure 19:
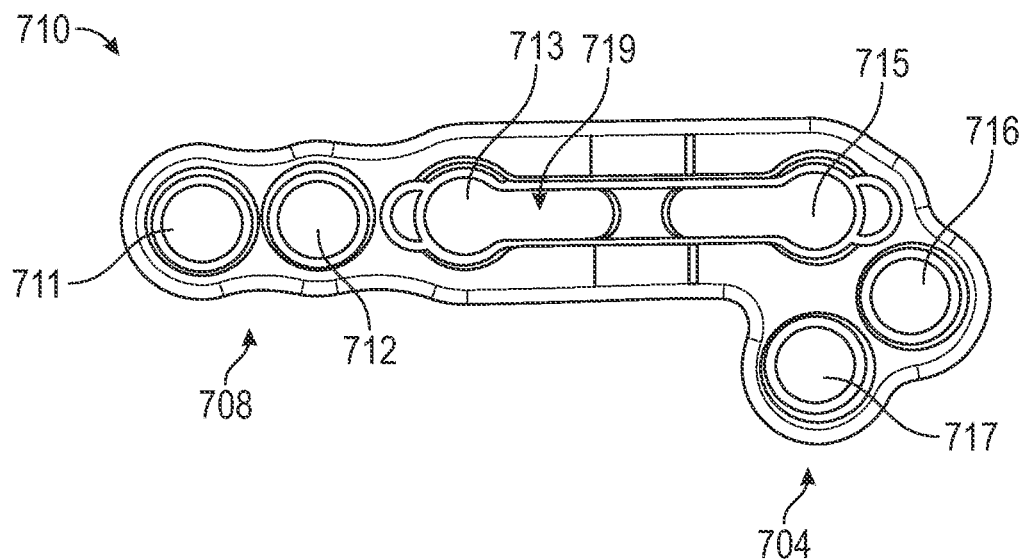
FIG. 19 shows a top view of a bone plate.
Figure 20:
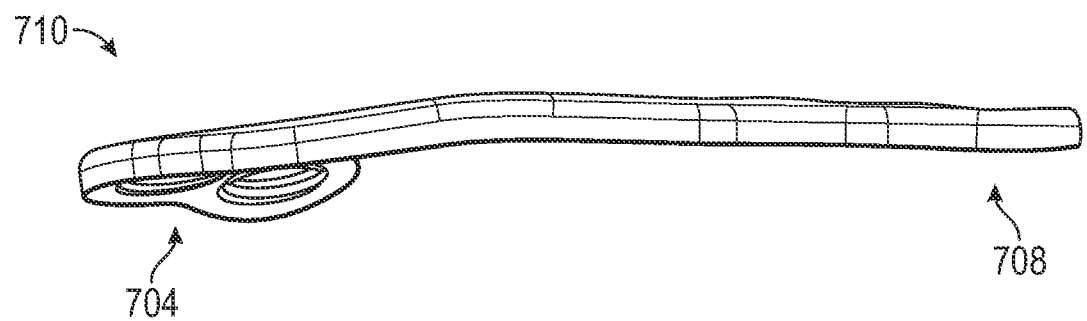
FIG. 20 shows a side view of the bone plate.

FIGS. 19-20 show further detail of the bone plate 710. The bone plate 710 can be contoured to fit against the medial cuneiform bone 104 and the metatarsal bone 108. The bone plate 710 can to be made out of titanium, aluminum, steel, or other suitable materials in the orthopedic field.

The first end 704 of the bone plate 710 can have a plurality of apertures 715, 716, 717. The apertures 716, 717 can be sized to receiver the fasteners 730. The aperture 715 can be sized to receive the prong 724 of the clip 720. The second end 708 of the bone plate 710 can have a plurality of apertures 711, 712, 713. The apertures 711, 712 can be sized to receive the fasteners 730. The aperture 713 can be sized to receive the prong 728 of the clip 720. The clip 720 can include a recess 719 for receiving, or at least partially receiving, the transverse member 726 of the clip 720. This can reduce the overall profile of the assembled bone plate assembly 700.

FIGS. 21-22 show the bone plate assembly 710 assembled with the patient's foot 100. The first end 704 of the bone plate 710 can be attached with the medial cuneiform bone 104 by the fasteners 730. The fasteners 730 can extend through the apertures 716, 717 and into the medial cuneiform bone 104. The second end 708 of the bone plate 710 can be attached with the metatarsal bone 108. The fasteners 730 can extend through the apertures 711, 712 and into the metatarsal bone 108. In some implementations, the fasteners 730 can be received within respective intersection points 320, 322, 324, and/or 326 of the k-wires 300. Alternatively, the fasteners can form new holes in the bones of the patient's foot.

The clip 720 can span across the joint between the medial cuneiform bone 104 and the metatarsal bone 108. The first prong 724 can be received within aperture 715 and into the metatarsal bone 108. The second prong 728 can be received through the aperture 713 and into the medial cuneiform bone 104. In certain implementations, the prongs 724, 728 can be received within the respective intersections 322, 324. The prongs 724, 728 can include a plurality of serrated edges for enhanced engagement features for attaching within the bones in the patient's foot 100.

In certain implementations, different alignment guides 200 can be used depending on the intended fixation means for the medial cuneiform bone 104 with the metatarsal bone 108. The different alignment guides 200 can include cannula that align the k-wires 300 at different points in the bone to match apertures in the different fixation means.

Virtual Modelling of Correction Factor

Figure 23:
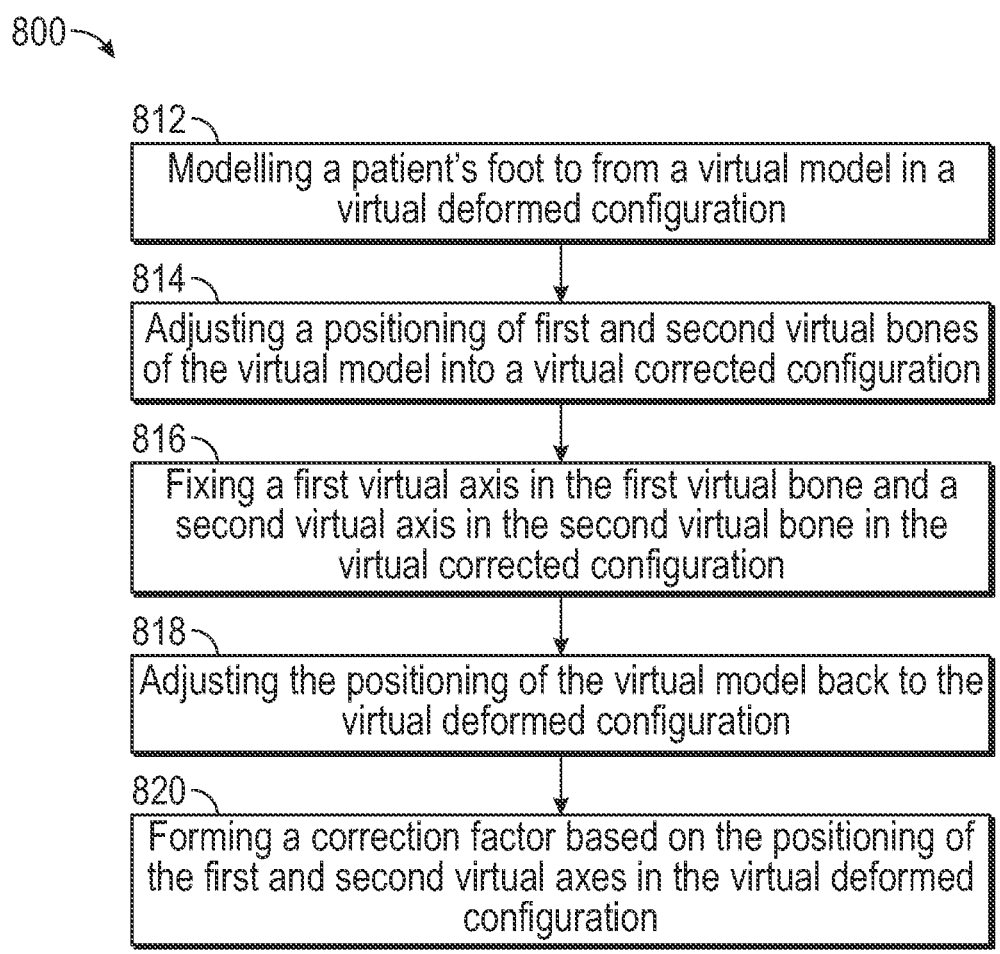
FIG. 23 shows a method of calculating a correction factor using a virtual model.
Figure 24A:
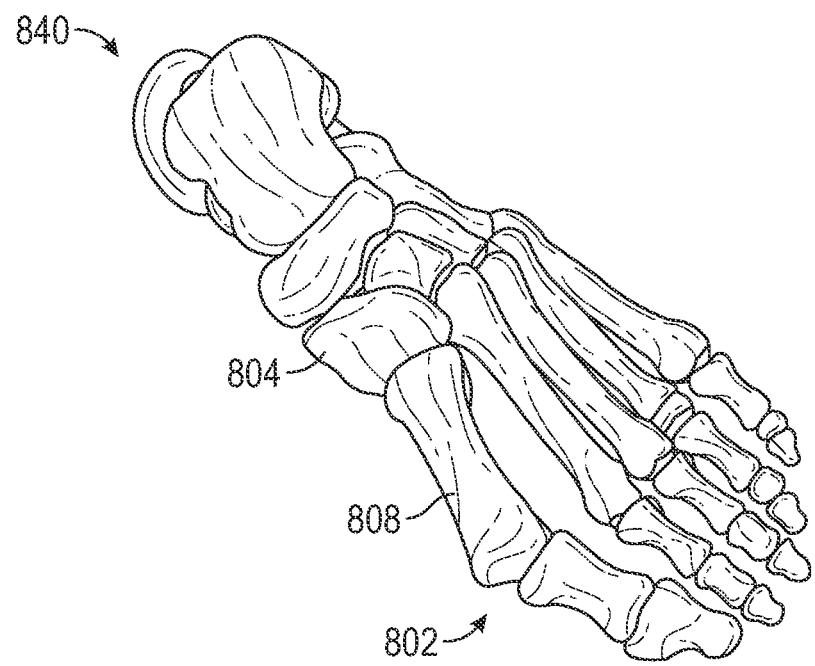
FIG. 24A shows the virtual model in a virtual deformed configuration.
Figure 24B:
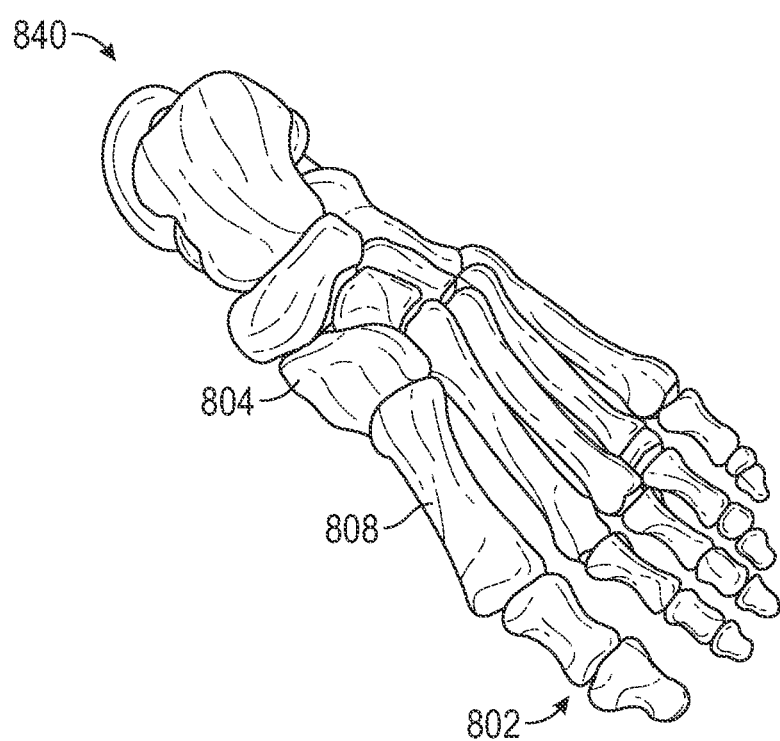
FIG. 24B shows the virtual model adjusted into a virtual corrected configuration.
Figure 24C:
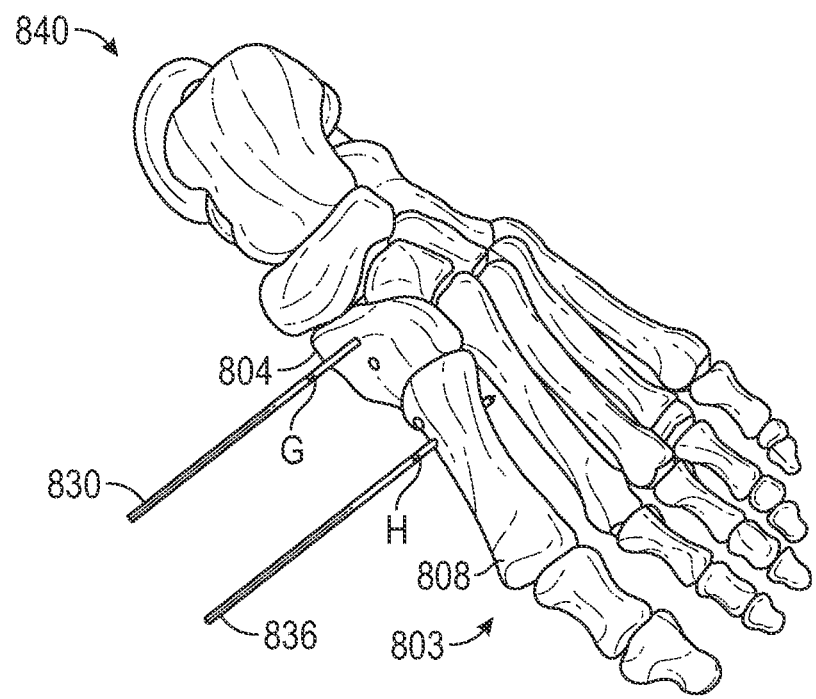
FIG. 24C shows fixing two virtual axes in a first virtual bone and a second virtual bone, respectively, in the virtual corrected configuration.
Figure 24D:
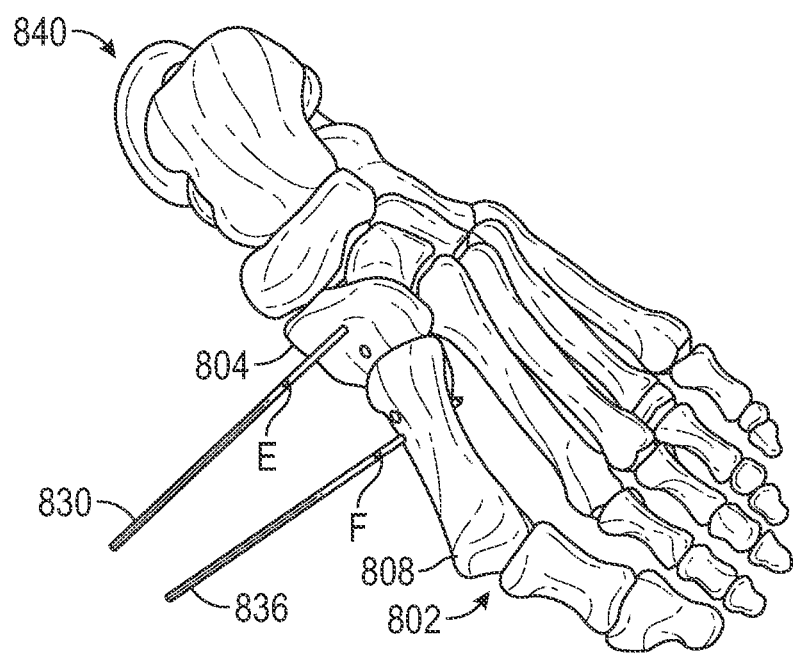
FIG. 24D shows the virtual model returned to the virtual deformed configuration with the resultant orientation of the two virtual axes defining a correction factor for the virtual model.
Figure 25:
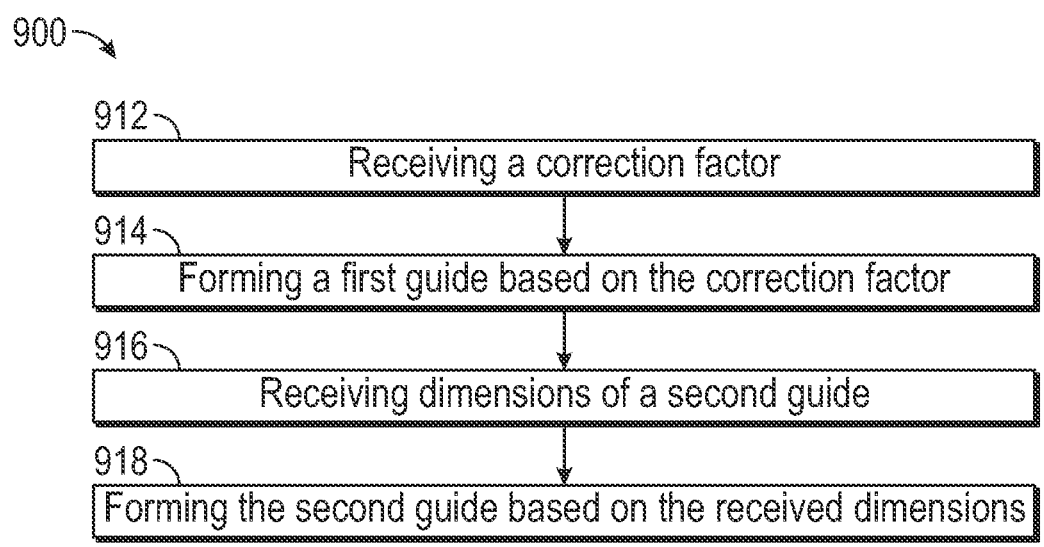
FIG. 25 shows a method of manufacturing an adjustment guide based on the correction factor.

FIG. 23 describes a process 800 for designing an alignment guide that customized to a patient's unique anatomy. Although described herein in the context of a patient's foot, the process 800 can be used for other parts of a patient's body. The process 800 is further illustrated in FIGS. 24A-24D. At step 812, a virtual model 840 of a patient's foot is created. The virtual model 840 can be based on a scan of a patient's foot including a deformity, such as a bunion and/or *Hallux valgus*. The scan used to create or render the virtual model 840 can be based on a CT, PET, X-ray, ultrasound, MRI, or other type of medical imaging scan.

The virtual model 840 can include virtual representations of the bones of the patient's foot. The virtual model 840 can include a virtual deformed configuration 802 of the patient's bones. The virtual model 840 can include a virtual first bone 804 and a virtual second bone 808. The virtual first bone 804 can correspond to a medial cuneiform bone in the patient's foot and the virtual second bone 808 can correspond to a metatarsal.

The virtual model 840 can be displayed to a user through a graphical user interface (e.g., on a computer). The virtual model 840 can be manipulable by a user. In some implementations, the virtual model 840 can approximate the natural connections (e.g., ligaments, cartilage, and/or muscles) between bones in the patient's foot. Accordingly, movements of one virtual bone can alter the location of connected virtual bones. In other implementations, the virtual bones of the model 840 can be freely moved and manipulated by a user. Accordingly, feasible re-positioning of the bones and resultant movements of connected virtual bones can be approximated based on the skill and knowledge of a user.

At step 814, a user adjusts the configuration of first and second virtual bones 804, 808 into a virtual corrected configuration 803. The virtual corrected configuration 803 can include correction of one or more deformities of the patient's foot. Adjustment into the virtual corrected configuration 803 can include changing relative angles and positions between the first and second virtual bones 804, 808. Moreover, the virtual corrected configuration 803 can include one or more overlapping portions of the first and second virtual bones 804, 808. One or more virtual resection planes 804a, 808a, can be identified by a user to remove overlapping portions of the first and second virtual bones 804, 808 or otherwise adjust the lengths and dimensions thereof.

At step 816, a first virtual axis 830 is added to intersect the first virtual bone 804. A second virtual axis 836 is added to intersect the second virtual bone 808. The first virtual axis 830 is fixed relative to the first virtual bone 804. The second virtual axis 836 is fixed relative to the second virtual bone 808. The first and second virtual axes 830, 836 can be aligned with the virtual model 840 at a location that is easily accessible during surgery of the patient's foot.

The first and second virtual axes 830, 836 are parallel with each other. Advantageously, the first and second virtual axes 830, 836 can be aligned with one or more of the virtual resection planes 804a, 808a. The first virtual axis 830 extends through a point G located in a virtual Cartesian coordinate system. The second virtual axis 836 extends through a point H located in the virtual Cartesian coordinate system.

At step 818, the first and second virtual bones 804, 808 are returned to the original deformed configuration 802 of the model 840. The first and second virtual axes 830, 836 are rotated to different angles and/or translated relative to each other into the deformed configuration 802 from the corrected configuration 803. In the deformed configuration 802, the first and second virtual axes 830, 836 can be defined as vectors passing through respective point E, F, respectively, within the virtual Cartesian coordinate system.

At step 820, the relative positions of the first and second virtual axes 830, 836 in the deformed configuration 802 can be used to define a correction factor for an alignment guide. The relative positions can include relative angles in two or more of the virtual Cartesian coordinate system planes (e.g., z-x, z-y, x-y). The relative angles can correspond to the α, β, and/or γ angles in the alignment guide (e.g., alignment guide 200 or the like). The relative positions of the first and second virtual axes 830, 836 can be based on the respective point E, F. The points E, F can correspond to the respective points A, B in the alignment guide (e.g., alignment guide 200 or the like). Thus, the dimensions of the virtual model 840 can be used to form the correction factor of an alignment guide for use in surgery on the patient's foot.

Furthermore, the relative positions of the first and second virtual axes 830, 836 in the corrected configuration 803 can be used to define dimensions of a correction guide. The points G, H can correspond to the respective points C, D in the correction guide (e.g., correction guide 500 or the like). The first and second virtual axes 830, 836 in the corrected configuration 803 can correspond to the parallel axes of the cannula in the correction guide.

Furthermore, the relative positions of the first and second virtual axes 830, 836 in the deformed configuration 802 can be used to define dimensions of a resection guide. The dimensions can include an orientation of a slot (e.g., slot 407) in the resection guide. The slot can be aligned parallel with one or more of the resection planes 804a, 808a. The resection guide can also include one or more apertures aligned with the first and/or second virtual axes 830, 836 in the deformed configuration 802.

As an alternative to creating the model 803, a user (e.g., a surgeon) could describe the angles (α, β, and/or γ) and/or translations needed to correct the deformities in the patient's foot 100. This description can be based on a user's knowledge and experience and/or in conjunction with viewing a scan of the patient's foot 100. The user-provided information can indicate the alignment guide 200 needed during in surgery. For example, a user can be provided a kit with multiple alignment guides and select among a pre-determined set of alignment guides 200 that each correct different, but commonly seen deformations in a patient's foot. In certain implementations, the alignment guide 200 can include multiple sets of cannula that correspond to different correction factors.

Manufacturing of Lapidus System

Process 900 is a method of manufacturing a system for correcting alignment in the patient's foot 100 based on a correction factor. At step 912, a manufacturer can receive a correction factor. The correction factor can define one or more dimensions of an alignment guide (e.g., alignment guide 200). The correction factor can be a CAD model, in some implementations. The dimensions can include orientation and positioning of one or more cannula therethrough. For example, the correction factor can be based on the process 800 described above and/or user-provided information. The correction factor can be customized to an individual patient's foot. Alternatively, the correction factor can be one of a standard set of commonly used correction factors.

At step 914, the manufacturer can form the alignment guide based on the correction factor. For example, the manufacture can 3D print the alignment guide.

At step 916, the manufacturer can receive dimensions for creating a correction guide. The dimensions for the correction guide can be based on the process 800 described above or otherwise customized to an individual patient's foot.

At step 918, the manufacturer can form the correction guide based on the received dimensions. For example, the manufacture can 3D print the correction guide.

Alternative Component Structures

Figure 26A:
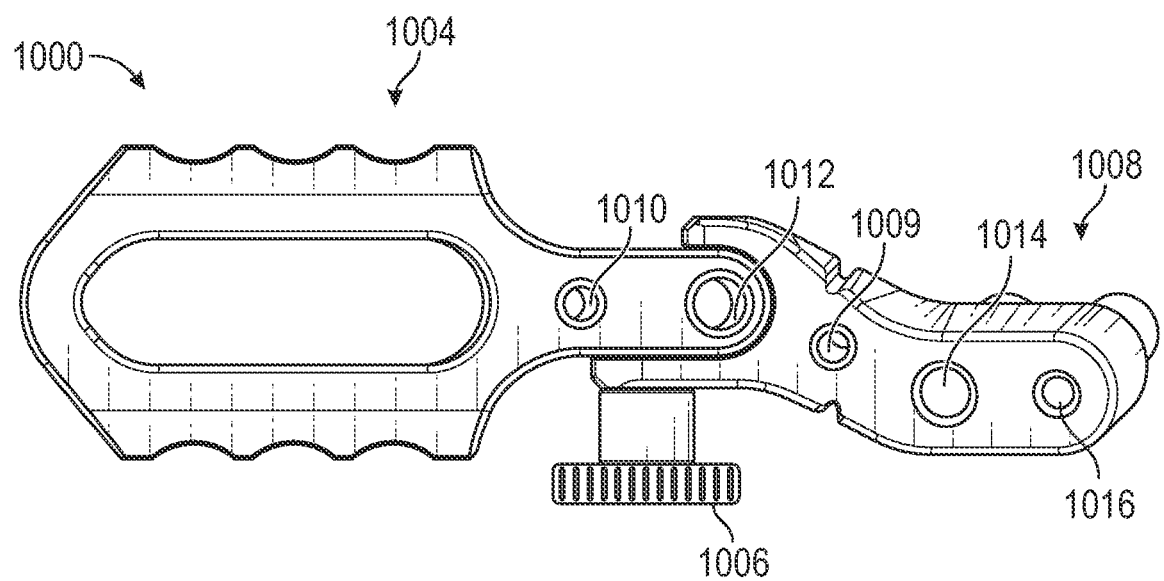
FIG. 26A shows a side view of another implementation of an alignment guide.
Figure 26B:
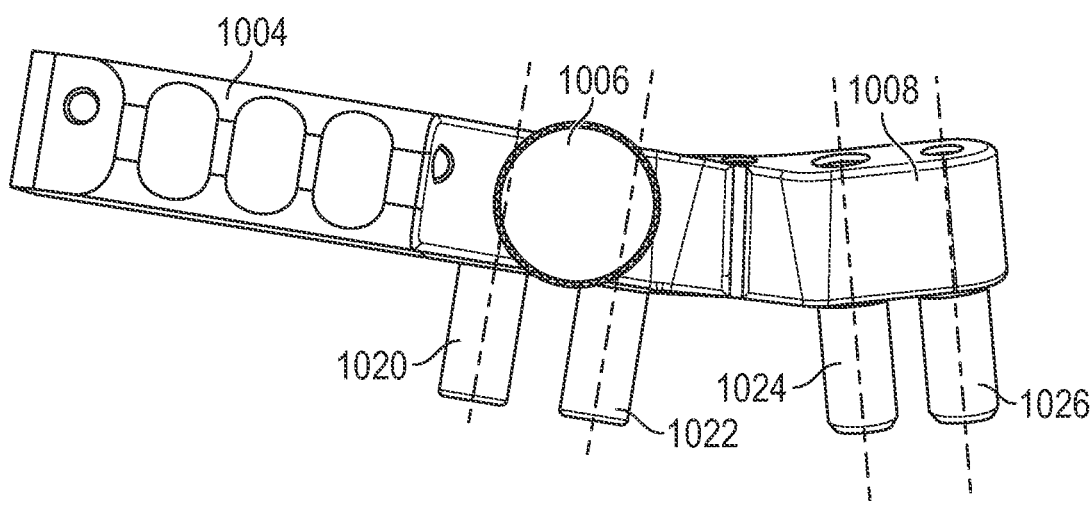
FIG. 26B shows a top view of the alignment guide of FIG. 26A.

FIGS. 26A-26B illustrate another possible configuration for an adjustment guide 1000. The adjustment guide 1000 can include the same features and functionalities of the adjustment guide 200 described above, including some of the differences noted below. The adjustment guide 1000 can include a first portion 1004 and a second portion 1008. The first portion 1004 can be releasably connectable with the second portion 1008. The first portion 1004 can include a handle 1004a. The handle portion 1004a can include an aperture therethrough. The handle portion 1004a can function to enable a user to easily hold the adjustment guide 1000 in place during use. The first portion 1004 of the adjustment guide 1000 can include one or more cannula 1010, 1012 extending therethrough. The cannula 1010, 1012 can extend through the first portion 1004. The cannula 1010, 1012 can extend along parallel axes 1020, 1022.

The second portion 1008 can include one or more cannula 1014, 1016. The cannula 1014, 1016 can extend through the second portion 1008. The cannula 1014, 1016 can extend along parallel axes 1024, 1026, respectively. The axes 1020, 1022 can be nonparallel with the axes 1024, 1026.

The first or second portions 1004, 1008 can include a centering cannula 1009. The centering cannula 1009 can be used to align the adjustment guide 1000 at the tarsometatarsal joint between the medial cuneiform bone 104 and the metatarsal 108.

Figure 27:
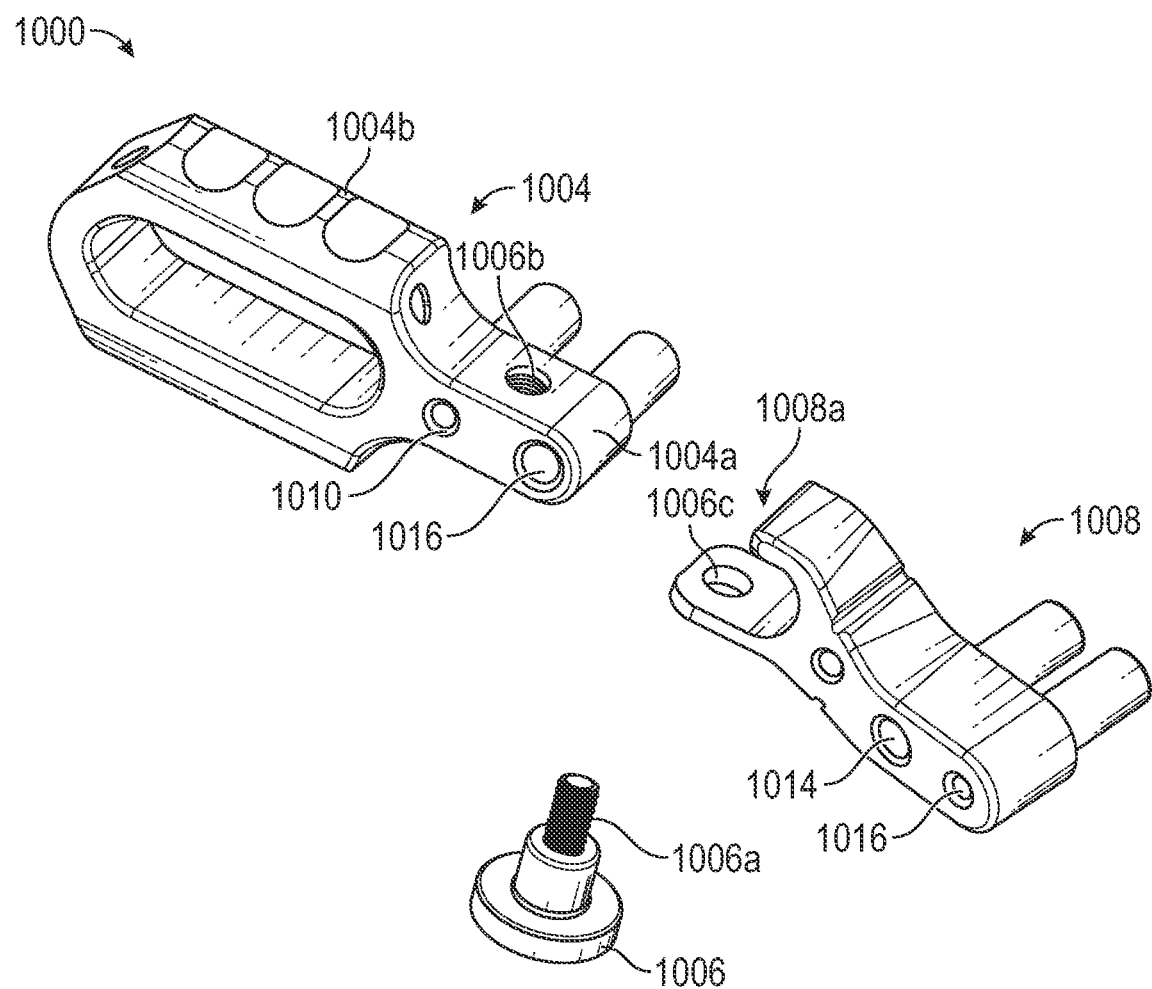
FIG. 27 shows an exploded view of the alignment guide of FIG. 26A.

As shown in FIG. 27, the first portion 1004 can be connectable with the second portion 1008 by an attachment mechanism 1006. The attachment mechanism 1006 can be a thumbscrew. As a thumbscrew, the attachment mechanism 1006 can include a threaded end 1006a. The attachment mechanism 1006 can extend through an aperture 1006b in the first portion 1004. The attachment mechanism 1006 can extend through an aperture 1006c in the second portion 1008. At least one of the apertures 1006b, 1006c can be internally threaded to couple with the threaded end 1006a. Accordingly, the first and second portions 1004, 1008 can be coupled together by the attachment mechanism 1006.

The second portion 1008 can include a recess 1008a. The first portion 1004 can include a projection portion 1004b. The projection portion 1004b can be received within the recessed portion 1008a. The recess/protrusion arrangement can enhance the stability of the coupling between the first portion 1004 and the second portion 1008.

Figure 28A:
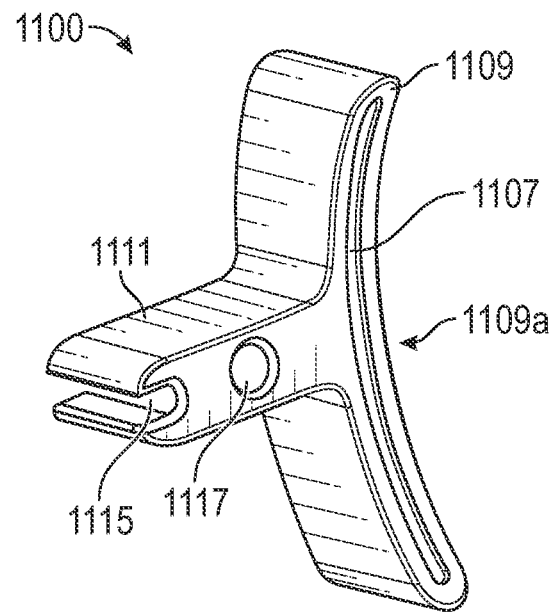
FIG. 28A shows a perspective view of another implementation of a resection guide.
Figure 28B:
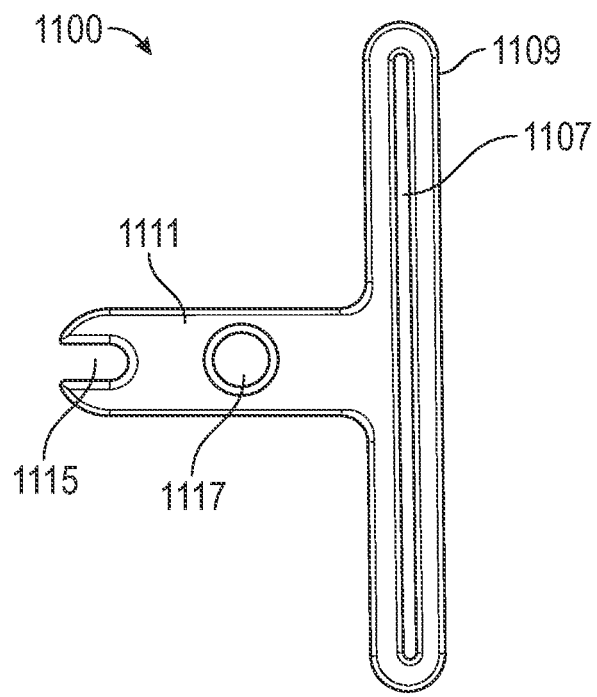
FIG. 28B shows a front view of the resection guide of FIG. 28A.

FIGS. 28A-28B show another implementation of a resection guide 1100. The resection guide 1100 can be structured similarly to the resection guide 404 described above, including some of the differences noted herein. The resection guide 1100 can include a first portion 1111. The first portion 1111 can include one or more apertures 1115, 1117 extending therethrough. The first portion 1111 can be coupled with a planar portion 1109. The planar portion 1109 can include a slots 1107 therein. The slot 1107 can be sized to allow a resection tool to extend therethrough for resecting a bone of a patient's body (e.g., the patient's foot 100). In some implementations, the planar portion 1109 can include a curved shape to allow the slot 1107 to be placed closer to and/or in contact with the patient's body. This can reduce error associated with the process of resecting a bone.

Figure 29:
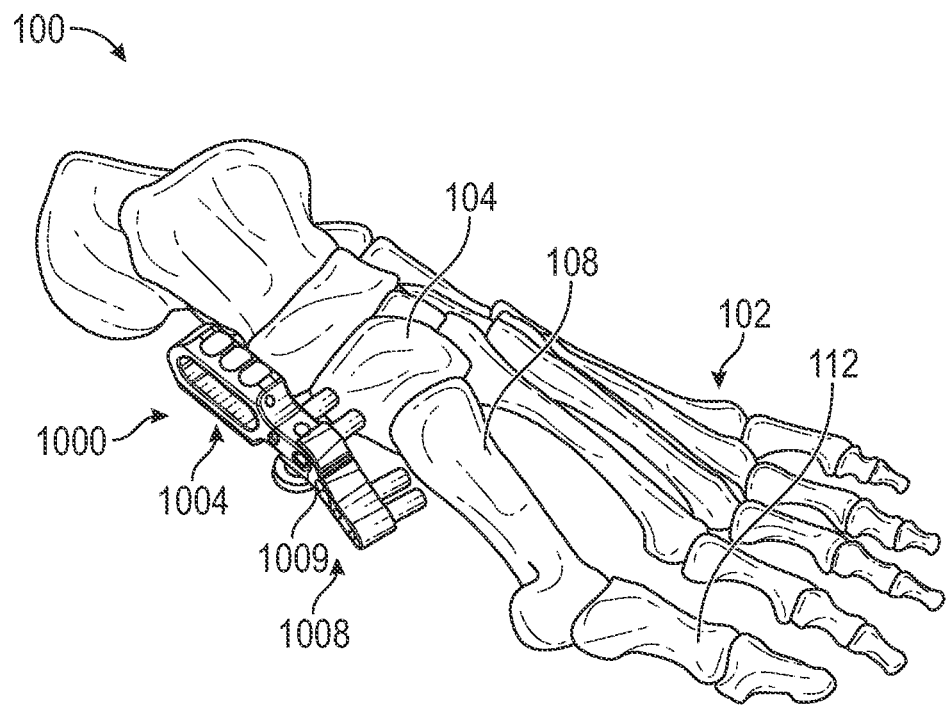
FIG. 29 shows alignment of the alignment guide of FIG. 26A with a patient's foot.
Figure 30:
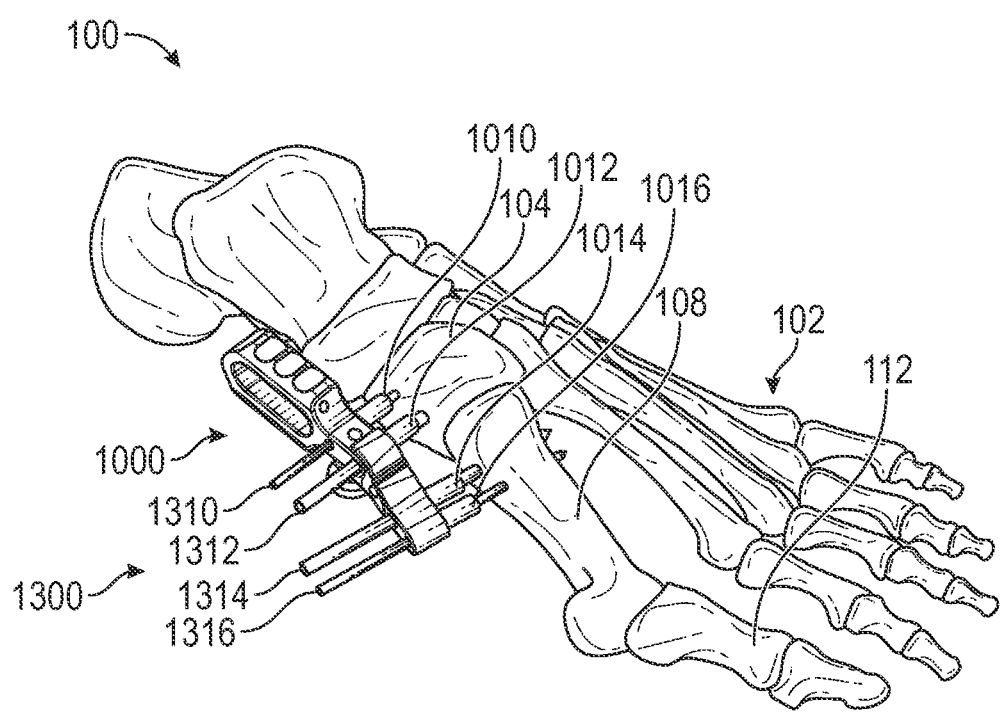
FIG. 30 shows insertion of a plurality of k-wires into a medial cuneiform bone and a metatarsal bone through the alignment guide.

FIG. 29 shows one method of using the adjustment guide 1100 in a procedure for correcting alignment between two bones in a patient's body. The adjustment guide 1000 can be used to correct alignment of a medial cuneiform bone 104 and a metatarsal bone 108 in a patient's foot 100. The process shown in FIGS. 29-34 is similar to and can include any of the steps and details described above in the process shown in FIGS. 1-22.

The centering cannula 1009 can align the adjustment guide 1000 at the tarsometatarsal joint between the medial cuneiform bone 104 and the metatarsal 108. A k-wire (not shown) can extend through the centering cannula 1009 and into the space between the medial cuneiform bone 104 and the metatarsal 108. The first end 1004 of the adjustment guide 1000 can be generally aligned with the medial cuneiform bone 104. The second end 1008 of the adjustment guide 1000 can be generally aligned with the metatarsal 108. As shown further in FIG. 30 a plurality of k-wires 1300 can be inserted through the respective cannula of the adjustment guide 1000 and into the medial cuneiform bone 104 and the metatarsal bone 108. A first k-wire 1310 can be received within the cannula 1010 and intersect the medial cuneiform bone 104. A second k-wire 1312 can be received through the cannula 1012. A third k-wire 1314 can be inserted through the cannula 1014 and into the metatarsal 108. A fourth k-wire 1316 can extend through the cannula 1016 into the metatarsal 108. The k-wires 1300 can extend along respective axes of the cannula of the adjustment guide 1000. Accordingly, the alignment guide can define the intersection angles of the k-wires 1300.

Figure 31:
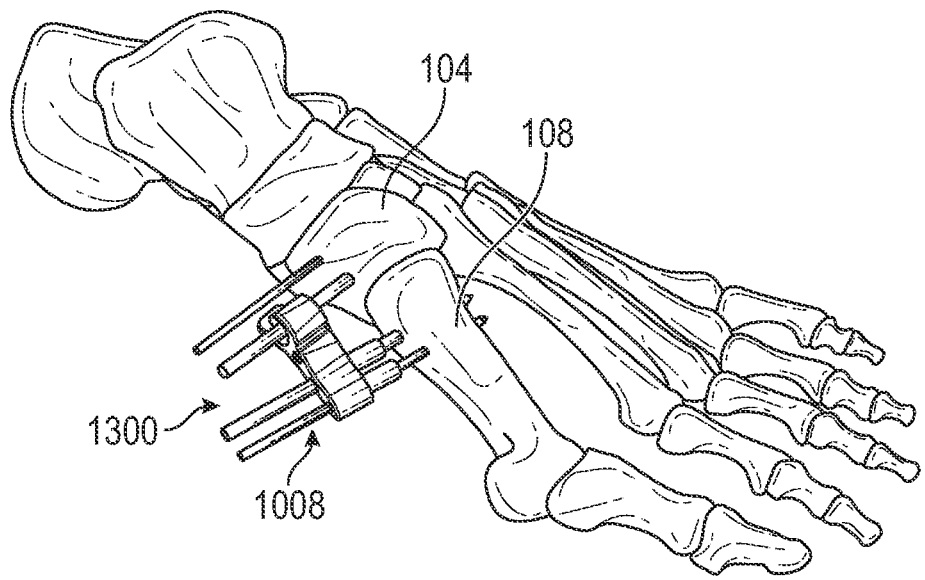
FIG. 31 shows a partial disassembly of the alignment guide.

As shown in FIG. 31, the first portion 1004 of the adjustment guide 1000 can be removed from the second portion 1008. The attachment mechanism 1006 can be removed from between the first portion 1004 and the second portion 1008. the first portion 1004 can be removed from the K wires 1300. The second portion 1008 can be removed from the k-wires 1300.

Figure 32:
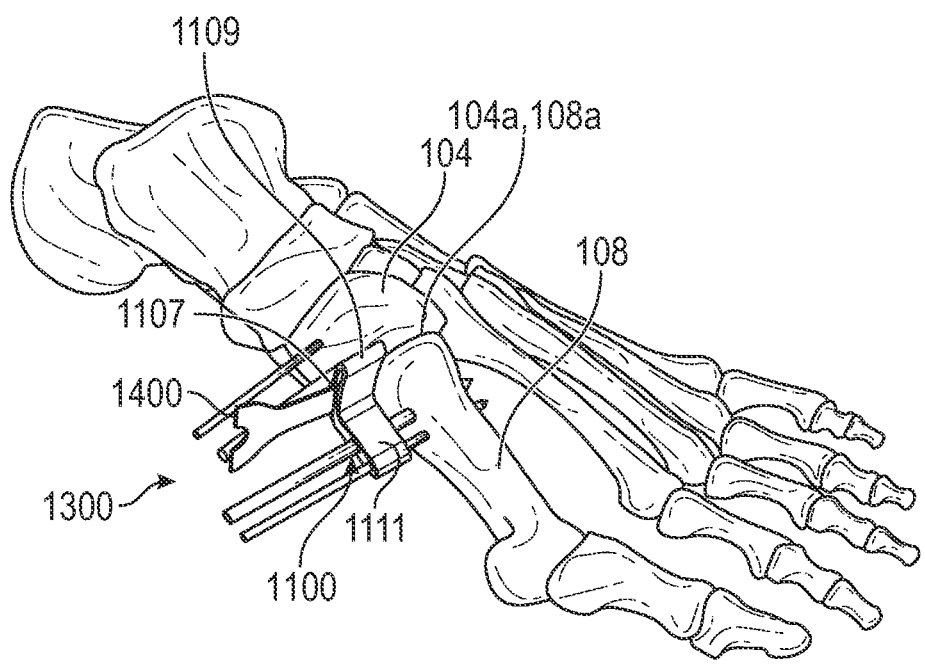
FIG. 32 shows the alignment guide removed and the installation of the resection guide of FIG. 28A.

As shown in FIG. 32, the resection guide 1100 can be slid over the k-wires 1300. The planar portion 1109 can be aligned with one or both of the medial cuneiform bone 104 and/or the metatarsal 108. A resection tool 1400 can be inserted through the slot 1107 to form resection planes 104a, and/or 108a on the respective medial cuneiform bone 104 and metatarsal 108. As described above, this can facilitate alignment of the medial cuneiform bone 104 and the metatarsal 108 in a corrected configuration 103.

Figure 33:
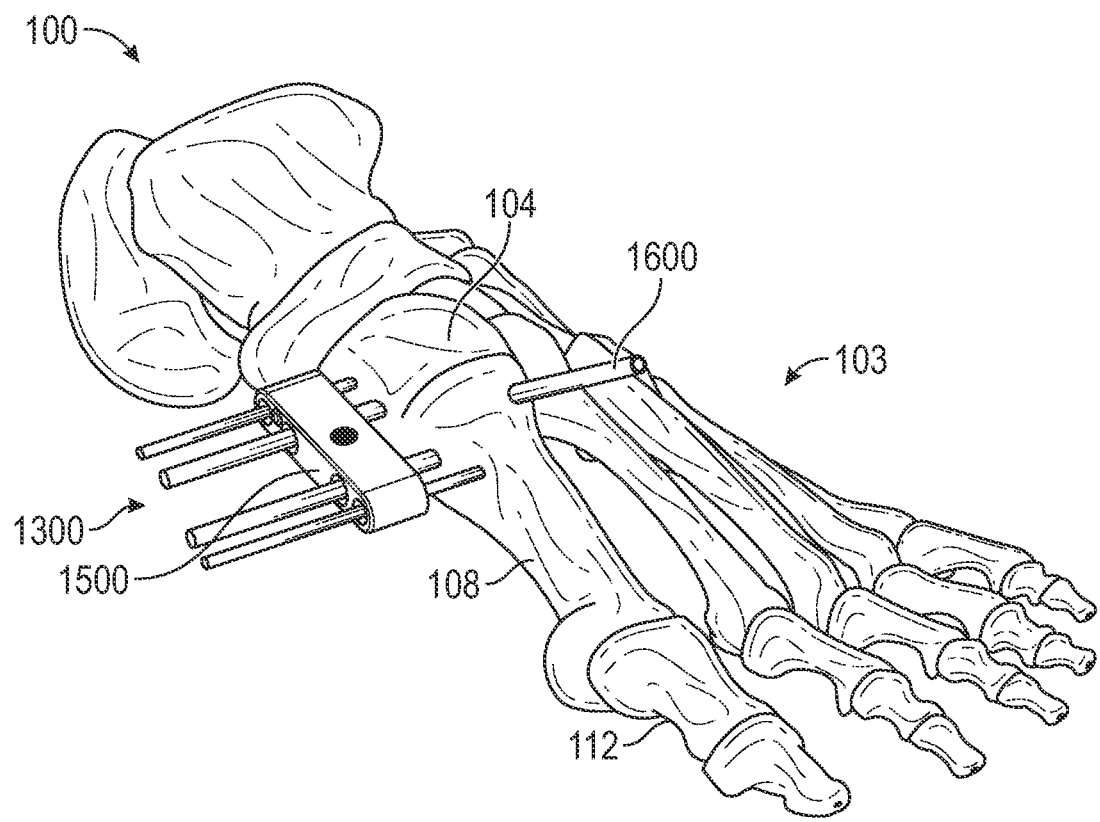
FIG. 33 shows a correction guide assembled over the plurality of k-wires to align the medial cuneiform bone and the metatarsal bone of the patient's foot into a corrected configuration and the insertion of a fixing k-wire.

As shown in FIG. 33, a correction guide 1500 can be slid over the k-wires 1300. The correction guide 1500 can be similar to the correction guide 500. The correction guide 1500 can include a plurality of cannula extending along parallel axes. The k-wires 1300 can be received in the cannula of the collection guide 1500. This can realign and adjust positions of the medial cuneiform bone 104, metatarsal 108 and/or the proximal phalanx 112 to form the corrected configuration 103 of the patient's foot 100.

Figure 34:
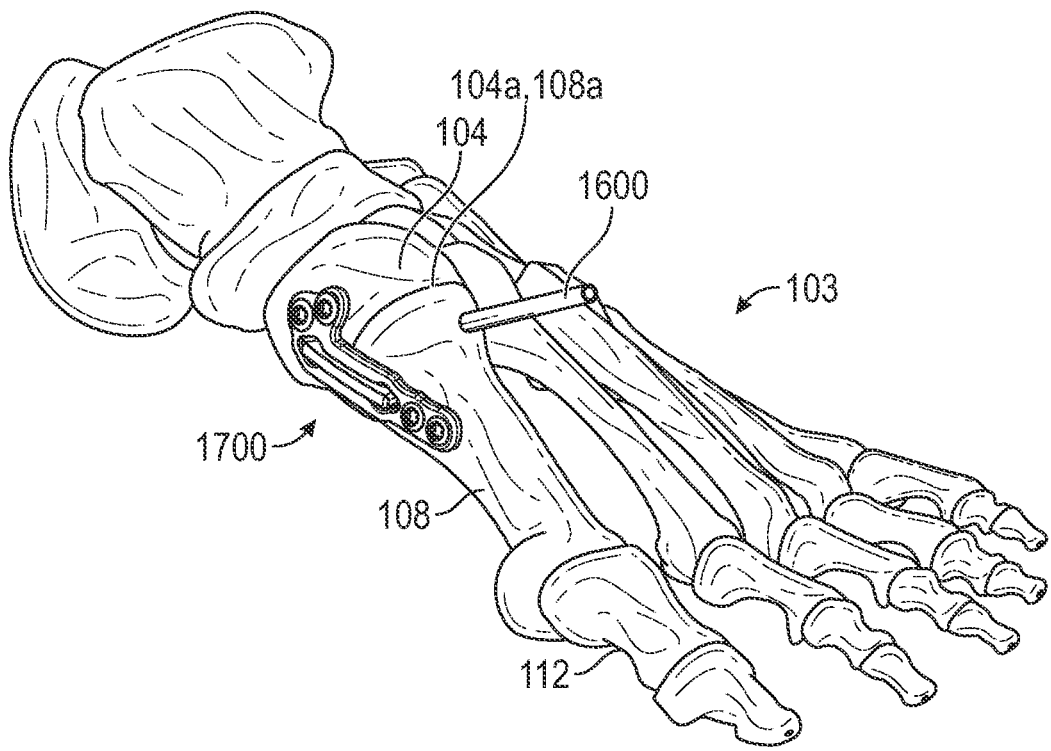
FIG. 34 shows a bone plate assembly assembled with the medial cuneiform bone and metatarsal bone in the corrected configuration.

In the corrected configuration 103, a fixing k-wire 1600 (or similar mechanism) can be inserted to fix the positions of the first metatarsal 108 and the medial cuneiform bone 104. As shown in FIG. 34, a bone plate assembly 1700, similar to the bone plate assembly 700, can be attached to the medial cuneiform bone 104 and the metatarsal 108 to maintain the relative positions of the two bones in the corrected configuration 103.

Certain Terminology

Terms of orientation used herein, such as "top," "bottom," "proximal," "distal," "longitudinal," "lateral," and "end," are used in the context of the illustrated example. However, the present disclosure should not be limited to the illustrated orientation. Indeed, other orientations are possible and are within the scope of this disclosure. Terms relating to circular shapes as used herein, such as diameter or radius, should be understood not to require perfect circular structures, but rather should be applied to any suitable structure with a cross-sectional region that can be measured from side-to-side. Terms relating to shapes generally, such as "circular," "cylindrical," "semi-circular," or "semi-cylindrical" or any related or similar terms, are not required to conform strictly to the mathematical definitions of circles or cylinders or other structures, but can encompass structures that are reasonably close approximations.

Conditional language, such as "can," "could," "might," or "may," unless specifically stated otherwise, or otherwise understood within the context as used, is generally intended to convey that certain examples include or do not include, certain features, elements, and/or steps. Thus, such conditional language is not generally intended to imply that features, elements, and/or steps are in any way required for one or more examples.

Conjunctive language, such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain examples require the presence of at least one of X, at least one of Y, and at least one of Z.

The terms "approximately," "about," and "substantially" as used herein represent an amount close to the stated amount that still performs a desired function or achieves a desired result. For example, in some examples, as the context may dictate, the terms "approximately," "about," and "substantially," may refer to an amount that is within less than or equal to 10% of the stated amount. The term "generally" as used herein represents a value, amount, or characteristic that predominantly includes or tends toward a particular value, amount, or characteristic. As an example, in certain examples, as the context may dictate, the term "generally parallel" can refer to something that departs from exactly parallel by less than or equal to 20 degrees. All ranges are inclusive of endpoints.

SUMMARY

Several illustrative examples of Lapidus procedure systems and methods have been disclosed. Although this disclosure has been described in terms of certain illustrative examples and uses, other examples and other uses, including examples and uses which do not provide all of the features and advantages set forth herein, are also within the scope of this disclosure. Components, elements, features, acts, or steps can be arranged or performed differently than described and components, elements, features, acts, or steps can be combined, merged, added, or left out in various examples. All possible combinations and subcombinations of elements and components described herein are intended to be included in this disclosure. No single feature or group of features is necessary or indispensable.

Certain features that are described in this disclosure in the context of separate implementations can also be implemented in combination in a single implementation. Conversely, various features that are described in the context of a single implementation also can be implemented in multiple implementations separately or in any suitable subcombination. Moreover, although features may be described above as acting in certain combinations, one or more features from a claimed combination can in some cases be excised from the combination, and the combination may be claimed as a subcombination or variation of a subcombination.

Any portion of any of the steps, processes, structures, and/or devices disclosed or illustrated in one example in this disclosure can be combined or used with (or instead of) any other portion of any of the steps, processes, structures, and/or devices disclosed or illustrated in a different example or flowchart. The examples described herein are not intended to be discrete and separate from each other. Combinations, variations, and some implementations of the disclosed features are within the scope of this disclosure.

While operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Additionally, the operations may be rearranged or reordered in some implementations. Also, the separation of various components in the implementations described above should not be understood as requiring such separation in all implementations, and it should be understood that the described components and systems can generally be integrated together in a single product or packaged into multiple products. Additionally, some implementations are within the scope of this disclosure.

Further, while illustrative examples have been described, any examples having equivalent elements, modifications, omissions, and/or combinations are also within the scope of this disclosure. Moreover, although certain aspects, advantages, and novel features are described herein, not necessarily all such advantages may be achieved in accordance with any particular example. For example, some examples within the scope of this disclosure achieve one advantage, or a group of advantages, as taught herein without necessarily achieving other advantages taught or suggested herein. Further, some examples may achieve different advantages than those taught or suggested herein.

Some examples have been described in connection with the accompanying drawings. The figures are drawn and/or shown to scale, but such scale should not be limiting, since dimensions and proportions other than what are shown are contemplated and are within the scope of the disclosed invention. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various examples can be used in all other examples set forth herein. Additionally, any methods described herein may be practiced using any device suitable for performing the recited steps.

For purposes of summarizing the disclosure, certain aspects, advantages and features of the inventions have been described herein. Not all, or any such advantages are necessarily achieved in accordance with any particular example of the inventions disclosed herein. No aspects of this disclosure are essential or indispensable. In many examples, the devices, systems, and methods may be configured differently than illustrated in the figures or description herein. For example, various functionalities provided by the illustrated modules can be combined, rearranged, added, or deleted. In some implementations, additional or different processors or modules may perform some or all of the functionalities described with reference to the examples described and illustrated in the figures. Many implementation variations are possible. Any of the features, structures, steps, or processes disclosed in this specification can be included in any example.

In summary, various examples of Lapidus procedure systems and related methods have been disclosed. This disclosure extends beyond the specifically disclosed examples to other alternative examples and/or other uses of the examples, as well as to certain modifications and equivalents thereof. Moreover, this disclosure expressly contemplates that various features and aspects of the disclosed examples can be combined with, or substituted for, one another. Accordingly, the scope of this disclosure should not be limited by the particular disclosed examples described above, but should be determined only by a fair reading of the claims.

What is claimed is:

1. A kit for correcting alignment between a first bone and a second bone by fusing a joint between the first bone and the second bone, the kit comprising:
   a first guide comprising:
   a first end portion having a first cannula aligned along a first axis;
   a second end portion having a second cannula aligned along a second axis, the first axis being non-parallel with the second axis;
   wherein the first guide is configured such that inserting a first k-wire through the first cannula intersects the first bone and inserting a second k-wire through the second cannula intersects the second bone when the first and second bones are in a deformed configuration;
   a second guide comprising:
   a first end portion having a first cannula; and
   a second end portion having a second cannula, the first cannula being parallel with the second cannula, wherein the first cannulas of the first and second guides have a respective first same diameter, and the second cannulas of the first and second guides have a respective second same diameter;
   wherein the second guide is configured such that when the first k-wire is fixed within the first bone and the second k-wire is fixed within the second bone in the deformed configuration, sliding the second guide over first and second k-wires, with the first and second k-wires being received within the respective first and second cannula of the second guide, re-aligns the first and second bones into a corrected configuration, and wherein the first guide and the second guide are separate structures.

2. The kit of claim 1, further comprising:
a stabilizing wire configured to be inserted into the first and second bone so as to fix the first and second bones in the corrected configuration.

3. The kit of claim 1, further comprising:
a bone plate, a first end configured to be attached with the first bone and a second end of the bone plate configured to be attached with the second bone such that the first and second bones are retained in the corrected configuration.

4. The kit of claim 3, further comprising a bone plate clip configured for insertion into the first and second bones in the corrected configuration.

5. The kit of claim 1, further comprising:
a first resecting guide configured to align a resecting tool with a resection location on the first bone.

6. The kit of claim 5, wherein the first resecting guide includes first and second cannula configured to be advanced over the first k-wire and a third k-wire, the third k-wire being parallel with the first k-wire.

7. The kit of claim 6, further comprising a second resecting guide configured to align the resecting tool with a resection location on the second bone.

8. The kit of claim 1, wherein the first end portion of the first guide includes a third cannula aligned parallel with the first cannula, the third cannula configured to receive a third k-wire that intersects the first bone.

9. The kit of claim 8, wherein the second end portion of the first guide includes a fourth cannula aligned parallel with the second cannula, the fourth cannula configured to receive a fourth k-wire that intersects the second bone.

10. The kit of claim 9, wherein the second guide includes third and fourth cannula, wherein the second guide is configured to be slid over the first and second k-wires, and the third and fourth k-wires are configured to be slid over the respective third and fourth cannula of the second guide to re-align the first and second bones into the corrected configuration.

11. The kit of claim 1, wherein the first and second cannula of the second guide are spaced a distance such that the first and second K-wires are configured to translate the first bone relative to the second bone into abutment in the corrected configuration when the first and second K-wires are received in the first and second cannula, respectively.

12. The kit of claim 1, wherein the first and second portions of the first guide are coupled together by an attachment mechanism.

13. The kit of claim 1, wherein the first guide includes a removable tube coupled with the first cannula.

14. The kit of claim 1, wherein the first axis and the second axis define a correction factor of the first guide.

15. The kit of claim 1, wherein the first same diameter is equal to the second same diameter.

16. The kit of claim 1, wherein the first same diameter is different than the second same diameter.

17. The kit of claim 1, wherein the first and second cannulas of the first guide are aligned along a first major length of the first guide, and the first and second cannulas of the second guide are aligned along a second major length of the second guide.

18. The kit of claim 17, wherein the first and second cannulas of the first guide have different diameters.

19. The kit of claim 18, wherein the first and second cannulas of the second guide have different diameters.

* * * * *